United States Patent
Fidler et al.

(10) Patent No.: US 7,344,829 B2
(45) Date of Patent: Mar. 18, 2008

(54) METHODS FOR DETECTING THE EFFICACY OF ANTICANCER TREATMENTS

(75) Inventors: Isaiah J. Fidler, Houston, TX (US); Corazon D. Bucana, Manvel, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 926 days.

(21) Appl. No.: 10/010,763

(22) Filed: Nov. 2, 2001

(65) Prior Publication Data

US 2002/0132275 A1    Sep. 19, 2002

Related U.S. Application Data

(60) Provisional application No. 60/245,745, filed on Nov. 3, 2000.

(51) Int. Cl.
```
C12Q 1/00      (2006.01)
G01N 33/53     (2006.01)
G01N 33/374    (2006.01)
G01N 33/567    (2006.01)
A61K 39/395    (2006.01)
```
(52) U.S. Cl. .................... 435/4; 435/7.1; 435/7.23; 435/7.21
(58) Field of Classification Search ............. 435/7.1, 435/4

See application file for complete search history.

(56) References Cited

OTHER PUBLICATIONS

Pollack et al (Proc. Annu Meet AACR, 1997, 38(A4249).*
Scardino et al (NCI monographs, 1988, 7:95-103).*
Prewett et al (J. Immunotherapy with Emphasis on Tumor Immunology, 1996, 19(6)419-427).*
Prewett et al (Clin. Can. Res., 1998, 4:2957-2966).*
Akiyama et al., "Growth factor and growth factor receptor localization in the hair follicle bulge and associated tissue in human fetus," *J. Invest. Dermatol.*, 106(3):391-396, 1996.
Bergler et al., "The expression of epidermal growth factor receptors in the oral mucosa of patients with oral cancer," *Arch. Otorhinolaryngol.*, 246(3):121-125, 1989.
Bergmann et al., "Insulin-like growth factor I overexpression in human pancreatic cancer. evidence for autocrine and paracrine roles," *Cancer Res.*, 55:2007-2011, 1995.
Bruns et al., "Blockade of the epidermal growth factor receptor signaling by a novel tyrosine kinase inhibitor leads to apoptosis of endothelial cells and therapy of human pancreatic carcinoma," *Cancer Res.*, 60:2926-2935, 2000.
Bruns et al., "In vivo selection and characterization of metastatic variants from human pancreatic adenocarcinoma by using orthotopic implantation in nude mice," *Neoplasia*, 1:50-62, 1999.
Chan et al., "A common human skin tumour is caused by activating mutations in β-catenin," *Nat. Genet.*, 21:410-413, 1999.
Ciardiello et al., "Antitumor activity of combined blockade of epidermal growth factor receptor and protein kinase A," *J. Nat'l Cancer Inst.*, 88:1770-1776, 1996.

Gill et al., "Monoclonal anti-epidermal growth factor receptor antibodies which are inhibitors of epidermal growth factor binding and antagonists of epidermal growth factor binding and antagonists of epidermal growth factor-stimulated tyrosine protein kinase activity," *J. Biol. Chem.*, 259:7755-7760, 1984.
Green and Couchman, "Differences in human skin between the epidermal growth factor receptor distribution detected by EGF binding and monoclonal antibody recognition," *J. Invest. Dermatol.*, 85(3):239-245, 1985.
Green and Couchman, "Distribution of epidermal growth factor receptors in rat tissues during embryonic skin development, hair formation, and the adult hair growth cycle," *J. Invest. Dermatol.*, 83(2):118-123, 1984.
Green et al., "Distribution and number of epidermal growth factor receptors in skin is related to epithelial cell growth," *Dev. Biol.*, 100:506-512, 1983.
Hansen et al., "Genetically null mice reveal a central role for epidermal growth factor receptor in the differentiation of the hair follicle and normal hair development," *Am. J. Pathol.*, 150(6):1959-1975, 1997.
Harmon et al., "Bisindolylmaleimide protein-kinase-C inhibitors delay the decline in DNA synthesis in mouse hair follicle organ cultures," *Skin Pharmacol.*, 10:71-78, 1997.
Korc et al., "Overexpression of the epidermal growth factor receptor in human pancreatic cancer is associated with concomitant increases in the levels of epidermal growth factor and transforming growth factor alpha," *J. Clin. Invest.*, 90:1352-1360, 1993.
Lokshin et al., "Mechanisms of growth stimulation by suramin in non-small-cell lung cancer cell lines," *Cancer Chemother Pharmacol.*, 43:341-347, 1999.
Luettcke et al., "The mouse waved-2 phenotype results from a point mutation in the EGF receptor tyrosine kinase," *Genes Dev.*, 8:399-413, 1994.
Maiorano and Favia, "Expression of phosphotyrosine in squamous cell carcinoma of the oral mucosa. Preliminary study," *Boll. Soc. Ital. Biol. Sper.*, 71(5-6):157-162, 1995.
Maiorano et al., "Prognostic implications of epidermal growth factor receptor immunoreactivity in squamous cell carcinoma of the oral mucosa," *J. Pathol.*, 185:167-174, 1998.
Murillas et al., "Expression of a dominant negative mutant of epidermal growth factor receptor in the epidermis of transgenic mice elicits striking alterations in hair follicle development and skin structure," *EMBO J.*, 14(21):5216-5223, 1995.
Nameda et al., "Endotoxin-induced L-arginine pathway produces nitric oxide and modulates the Ca2+ activated K+ channel in cultured human dermal papilla cells," *J. Invest Dermatol.*, 106:342-345, 1996.

(Continued)

*Primary Examiner*—Susan Ungar
(74) *Attorney, Agent, or Firm*—Fulbright & Jaworski L.L.P.

(57) ABSTRACT

Methods for determining the effectiveness of anticancer agents by determining and comparing growth factor receptor phosphorylation levels in samples obtained by non-invasive procedures before and after anticancer treatments are provided. The invention also provides methods for detecting growth factor receptor phosphorylation in hair follicles and other tissues obtained by non-invasive means.

16 Claims, 8 Drawing Sheets
(7 of 8 Drawing Sheet(s) Filed in Color)

OTHER PUBLICATIONS

Saleh et al., "Combined modality therapy of A431 human epidermoid cancer using anti-EGFr antibody C225 and radiation," *Cancer Biother. Radiopharm*, 14:451-463, 1999.

Smythe et al., "The activity of HMG-CoA reductase and acetyl-CoA carboxylase in human apocrine sweat glands, sebaceous glands, and hair follicles is regulated by phosphorylation and by exogenous cholesterol," *J. Invest. Dermatol.*, 111:139-148, 1998.

van Oijen et al., "Increased expression of epidermal growth factor receptor in normal epithelium adjacent to head and neck carcinomas independent of tobacco and alcohol abuse," *Oral Dis.*, 4(1):4-8, 1998.

Wagner et al., "Suppression of fibroblast growth factor receptor signaling inhibits pancreatic cancer growth in vitro and in vivo," *Gastroenterology*, 114:798-807, 1998.

Wang, et al., "Effects of in vivo treatments of nicotine and benzo[a]pyrene on the epidermal growth factor receptor in hamster buccal pouch," *Toxicology*, 107:31-38, 1996.

Wang et al., "Identification of epidermal growth factor receptor in human buccal mucosa," *Arch. Oral Biol.*, 35(10):823-828, 1990.

Whitcomb et al., "Immunohistochemical mapping of epidermal growth-factor receptors in normal human oral soft tissue," *Arch. Oral Biol.*, 38(9):823-826, 1993.

Yamada et al., "Evaluation of epidermal growth factor receptor in squamous cell carcinoma of the oral cavity," *Oral. Surg. Oral Med. Oral Pathol.*, 73:67-70, 1992.

Yamanaka et al., "Coexpression of epidermal growth factor receptor and ligands in human pancreatic cancer is associated with enhanced tumor aggressiveness," *Anticancer Res.*, 13:565-569, 1993.

Yamanaka et al., "Overexpression of HER2/neu oncogene in human pancreatic carcinoma," *Hum. Pathol.*, 24:1127-1134, 1993.

Albanell et al., "Pharmacodynamic studies of the specific oral EGFR tyrosine kinase inhibitor (EGFR-TKI) zd1839 ('Iressa') in skin from cancer patients partcipating in phase I trials: histopathological and molecular consequences of receptor inhibition," *European Journal of Cancer*, 37(Supp. 6): S159, 2001.

Parker et al., "Preferential activation of the epidermal growth factor receptor in human colon carcinoma liver metastases in nude mice," *J. of Histochemistry and Cytochemistry*, 46(5):595-602, 1998.

Pollack et al., "Inhibition of epidermal growth factor receptor-associated tyrosine phosphorylation in human carcinomas with CP-358,774: dynamics of receptor inhibition in situ and antitumor effects in athymic mice," *J. Pharmacology and Experimental Therapeutics*, 291(2):739-748, 1999.

\* cited by examiner

+ DAPI

METHODS FOR DETECTING THE EFFICACY OF ANTICANCER TREATMENTS

This application claims benefit of priority to U.S. Provisional Application Ser. No. 60/245,745, filed Nov. 3, 2000 now abandoned, the entire contents of which is incorporated by reference.

The government owns rights in the present invention pursuant to grant numbers R35-CA42107 and CA67952 from the National Cancer Institute, National Institutes of Health; by the Marc Lustgarten Foundation for Pancreatic Cancer Research. This work was further supported in part by Cancer Center Support Core grant CA16672, and by Habilitationsstipendium of the "Lise-Meitner-Programm" of the Ministerium für Wissenschaft und Forschung, Nord-Rhine-Westphalia, Germany.

BACKGROUND OF THE INVENTION

1. Field of the Invention

The present invention relates generally to the fields of cancer treatment. More particularly, it concerns non-invasive methods for determining the effectiveness of cancer treatment.

2. Description of Related Art

Methods of treating cancer include radiation therapy, surgery and chemotherapy. While chemotherapy has been widely employed, the indicated chemotherapeutic agents or combinations thereof are not always successful in achieving remission. All too often, an indicated course of chemotherapy is initiated, only to result in a failure to achieve remission of the cancer. The chemotherapy may continue for weeks or even months before the physician may conclude that the treatment is unsuccessful, and that alternative chemotherapeutic agents are warranted. Valuable time is lost during the period of ineffective chemotherapy.

Tumor cells generally express more growth factor receptors than normal cells. Chemotherapeutic drugs typically used to treat cancers and metastases are those that inhibit phosphorylation of the growth factor receptors. Some examples are drugs such as Novartis PKI166 or the Mendelsohn C225 antibody that inhibit phosphorylation of the epidermal growth factor receptor (EGF-R). Currently the only way to assay effectiveness of these treatment types is by performing biopsies, which is an invasive procedure and can result in complications from anesthesia and can further cause infections in the already immunocompromised patients. For example, Gewirtz and Calabretta (U.S. Pat. No. 5,427,916) discuss a method for predicting the effectiveness of antineoplastic therapy by comparing the expression of growth-regulated genes in neoplastic cells taken from a patient before and shortly after the initiation of therapy. Thus, an effective, non-invasive method for assessing the effectiveness of anticancer treatments is required.

SUMMARY OF THE INVENTION

The present invention overcomes these and other drawbacks in the art by providing non-invasive methods for determining the efficacy of anticancer treatments. Provided are methods for determining the effectiveness of anticancer agents by determining and comparing growth factor receptor phosphorylation levels in samples obtained by non-invasive procedures before and after anticancer treatments.

Several tissue samples types that may be obtained by non-invasive methods are described herein. In some specific examples the samples may be hair follicle cells, buccal mucosa cells, skin scrapings, bladder wash cells, pap-smear samples and the like.

Provided herein are also novel methods to determine growth factor receptor phosphorylation in a hair follicle.

Provided herein is a method for determining the effectiveness of a cancer treatment comprising (a) obtaining a tissue sample by non-invasive procedures from a patient undergoing the cancer treatment; and (b) determining growth factor receptor phosphorylation in said tissue before and after the cancer treatment. The control herein is the amount of growth factor receptor in the sample before the cancer treatment. The growth factor receptor for which phosphorylation is determined can be an epidermal growth factor receptor (EGFR), a fibroblast growth factor receptor (FGFR), an acidic fibroblast growth factor receptor, a basic fibroblast growth factor receptor, an insulin like growth factor receptor (IGFR), an insulin growth factor (IGF), a nerve growth factor receptor (NGFR), a transforming growth factor α receptor (TGF-αR), a transforming growth factor β receptor (TGF-βR), a neuregulin/heregulin receptor, a betacellulin receptor, a amphiregulin receptor, a heparin binding EGF-like growth factor receptor, or a cytokine growth factor receptor. As used herein, the term "cytokine" is meant to include molecules such as but are not limited to, interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interferon α (IFNα), interferon β. (IFNβ), interferon γ, (IFNγ), tumor necrosis factor α. (TNFα), tumor necrosis factor β (TNFβ), granulocyte colony stimulating factor (G-CSF), and granulocyte/macrophage colony stimulating factor (GM-CSF).

The tissue sample that is obtained by non-invasive means can be a hair follicle, buccal mucosa cells/tissue, a pap-smear sample, bladder-wash cells, skin scrapings and other similar cell samples. Non-invasive means procedures are defined herein as procedures that do not require surgery.

The invention also provides methods for determining growth factor receptor phosphorylation which comprise the general steps of (a) obtaining a sample comprising the growth factor receptor; (b) contacting the sample with an antibody; and (c) detecting the bound antibody.

The antibody used can be any anti-phosphorylated growth factor receptor antibody. In alternative embodiments the antibody may be an anti-phosphotyrosine antibody, an anti-phosphoserine antibody or and anti-phosphothreonine antibody. The antibody can further comprises a detectable label. In one embodiment, the method has a second antibody that comprises a detectable label which is contacted with the first antibody prior to the detection.

Almost any detectable label known to the skilled artisan may be used. In specific embodiments the detectable label is selected from a group comprising a fluor, an enzyme, a chemiluminescent label, or a radionuclide. Examples of fluors include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red. Fluors can be detected by immunoflourescence and quantitated by methods known in the art. For example the optical density may be determined and software such as Optimas Image Analysis can be used. Examples of enzymatic labels include horseradish peroxidase, urease, or alkaline phosphatase to mention a few and colorimetric indicator substrates can be employed to provide a detection means which can be quantitated spectrophotometrically. Examples of radoinuclides include the radioisotopes $^{32}P$, $^{14}C$, $^{125}I$, $^{3}H$, and $^{131}I$.

The methods of the invention are contemplated useful in cancer patients afflicted with any cancer type. Specifically the patient may have cancer of the breast, prostrate, colon, pancreas, head and neck, bladder, blood, bone, bone marrow, brain, esophagus, gastrointestine, brain, kidney, liver, lung, nasopharynx, ovary, skin, stomach, or uterus.

Additional embodiments contemplate analyzing the growth factor receptors for phosphorylation at multiple time points during the cancer therapy. Additionally multiple tissues from a single patient may be analyzed as well. The inventors also contemplate automating the methods.

The invention also provides methods for detecting growth factor receptor phosphorylation in hair follicles, comprising (a) preparing a hair follicle; (b) incubating the hair follicle with an anti-phosphorylated growth factor receptor antibody; (c) incubating the composition of step (b) with a second antibody which comprises a detectable label; and (d) detecting the binding of the antibodies of steps (b) and (c) to the growth factor receptor. The growth factor receptor can be an epidermal growth factor receptor, a fibroblast growth factor receptor, an acidic fibroblast growth factor receptor, a basic fibroblast growth factor receptor, an insulin like growth factor receptor, a nerve growth factor receptor, a transforming growth factor α receptor, a transforming growth factor β receptor, an insulin growth factor (IGF), a neuregulin receptor, a betacellulin receptor, a amphiregulin receptor, a heparin binding EGF-like growth factor receptor, or a cytokine growth factor receptor. As used herein, the term "cytokine" is meant to include molecules such as but are not limited to, interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interferon α (IFNα), interferon β. (IFNβ), interferon γ, (IFNγ), tumor necrosis factor α. (TNFα), tumor necrosis factor β (TNFβ), granulocyte colony stimulating factor (G-CSF), and granulocyte/macrophage colony stimulating factor (GM-CSF). In specific embodiments the growth factor receptor is epidermal growth factor receptor.

The invention also provides kits for determining the effectiveness of treatment of cancer with anticancer agents, said kit comprising in a suitable container means (a) components for extracting samples by non-invasive means before and after administration of an anticancer agent; (b) components for determining phosphorylation states of growth factor receptors in the samples.

Another aspect of the invention provides a method of cancer therapy comprising the steps of (a) determining the effectiveness of a cancer treatment in a patient by the method of claim 1; (b) determining the need for a different cancer treatment based on the effectiveness; and (c) administering the different cancer treatment to the patient. The cancer treatment that the patient is undergoing can be one which results in changes in growth factor receptor phosphorylation. The change can be a decrease or an increase in the growth factor receptor phosphorylation. The growth factor receptor can be an epidermal growth factor receptor, fibroblast growth factor receptor, acidic fibroblast growth factor receptor, basic fibroblast growth factor receptor, insulin like growth factor receptor, nerve growth factor receptor, transforming growth factor α receptor, transforming growth factor β receptor, a neuregulin receptor, a betacellulin receptor, a amphiregulin receptor, a heparin binding EGF-like growth factor receptor, or a cytokine growth factor receptor.

In some embodiments the cancer treatment can be a chemotherapy treatment. In some aspects the chemotherapeutic agent changes the phosphorylation of a growth factor receptor. In one such example the chemotherapeutic agent is a protein kinase inhibitor. In one embodiment the protein kinase inhibitor is a tyrosine kinase inhibitor. In one specific embodiment the chemotherapeutic agent is PKI166. In another specific embodiment the tyrosine kinase inhibitor is the C225 antibody. In yet other embodiments the protein kinase inhibitor can be an antibody against any of the growth factor receptors. In another embodiment the protein kinase inhibitor is a serine or threonine kinase inhibitor.

The patient can have breast, prostrate, colon, pancreatic, head and neck, renal, bladder, blood, bone, bone marrow, brain, esophagus, gastrointestinal, brain, kidney, liver, lung, nasopharynx, ovary, skin, stomach, or uterine cancer.

The invention also provides methods for screening candidate drugs that modulate growth factor receptor phosphorylation comprising (a) administering a candidate drug to a non-human animal; (b) obtaining a sample by non-invasive means; c) determining the phosphorylation state of a growth factor receptor in said sample wherein a change in the phosphorylation of said growth factor receptor, as compared to the phosphorylation of the growth factor receptor from the same tissue in a non-human animal of the same species, identifies said candidate drug as a modulator of growth factor receptor phosphorylation.

As used herein the specification, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

The patent or application file contains at least one drawing executed In color. Copies of this patent or patent application publication with color drawing(s) will be provided by the Office upon request and payment of the necessary fee.

DESCRIPTION OF ILLUSTRATIVE EMBODIMENTS

Figure 1:
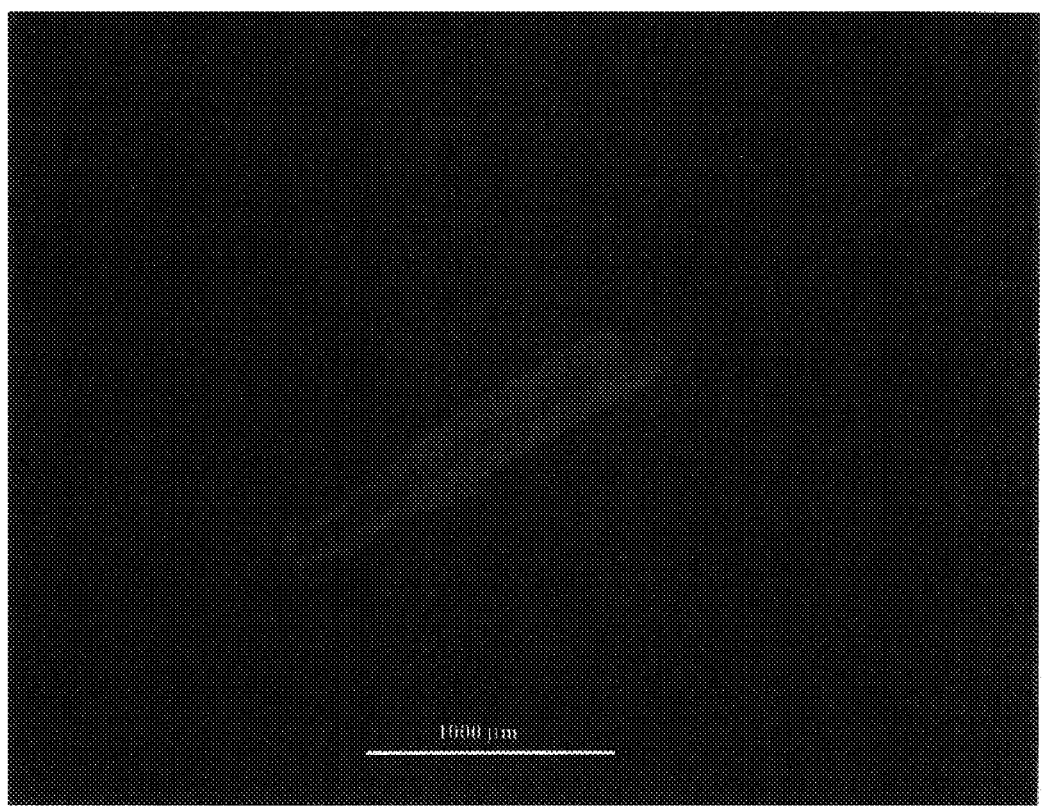
FIG. 1—Shows location of nuclei in one hair follicle where the bulb is not completely removed but the outer sheath just above it is intact.
Figure 2:
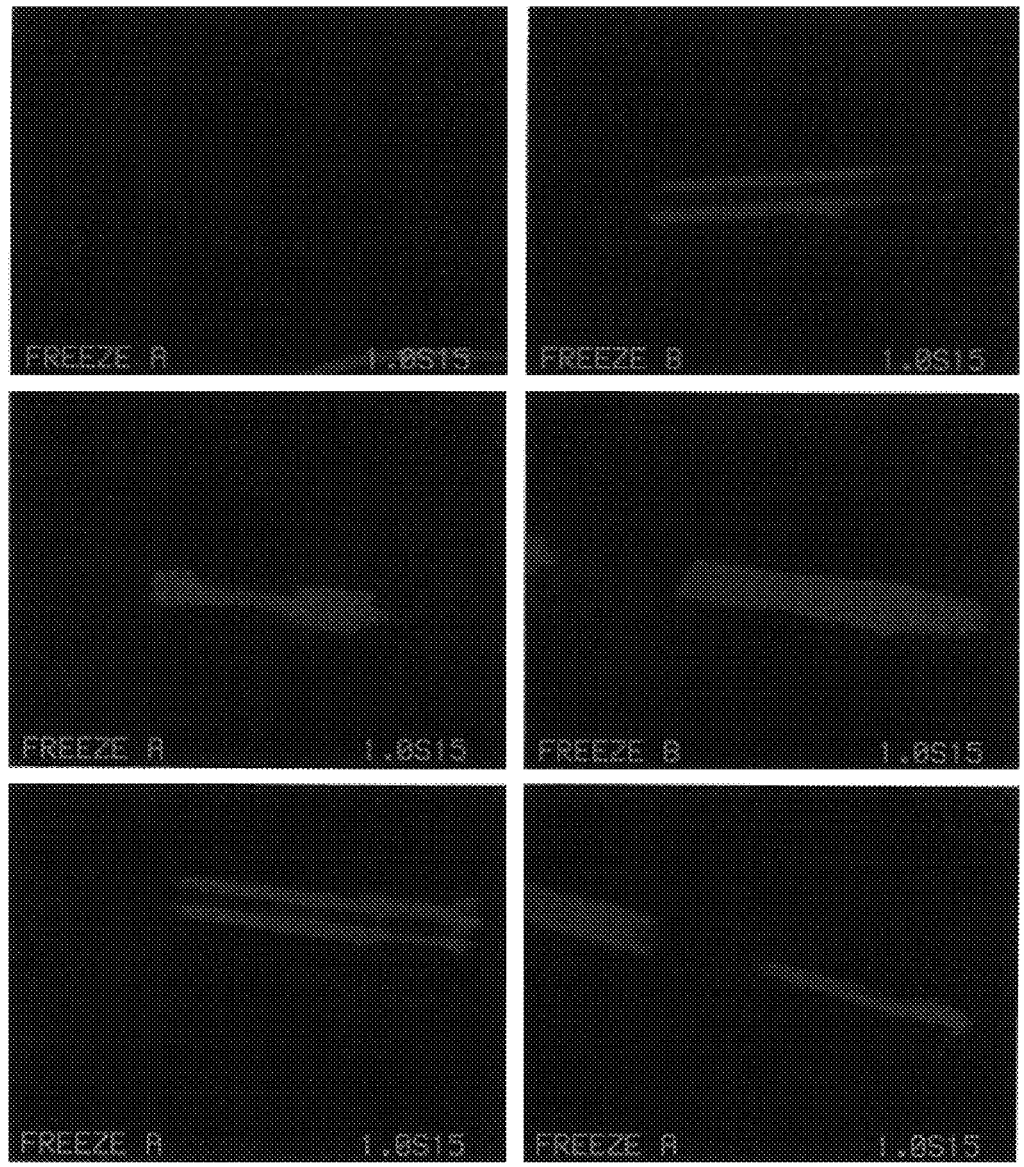
FIG. 2—Depicts several hair follicles with staining for activated (phosphorylated) EGF-R.
Figure 3:
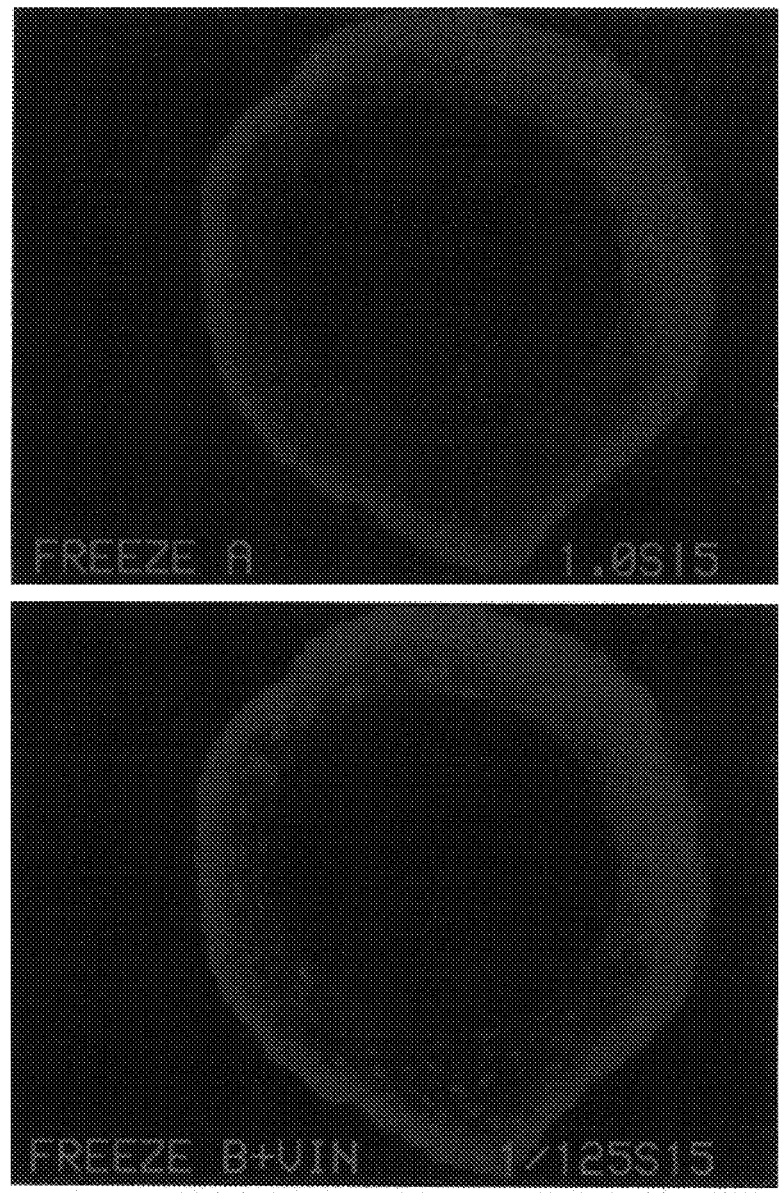
FIG. 3—Depicts that both primary and secondary antibodies penetrate outer root sheath.
Figure 4:
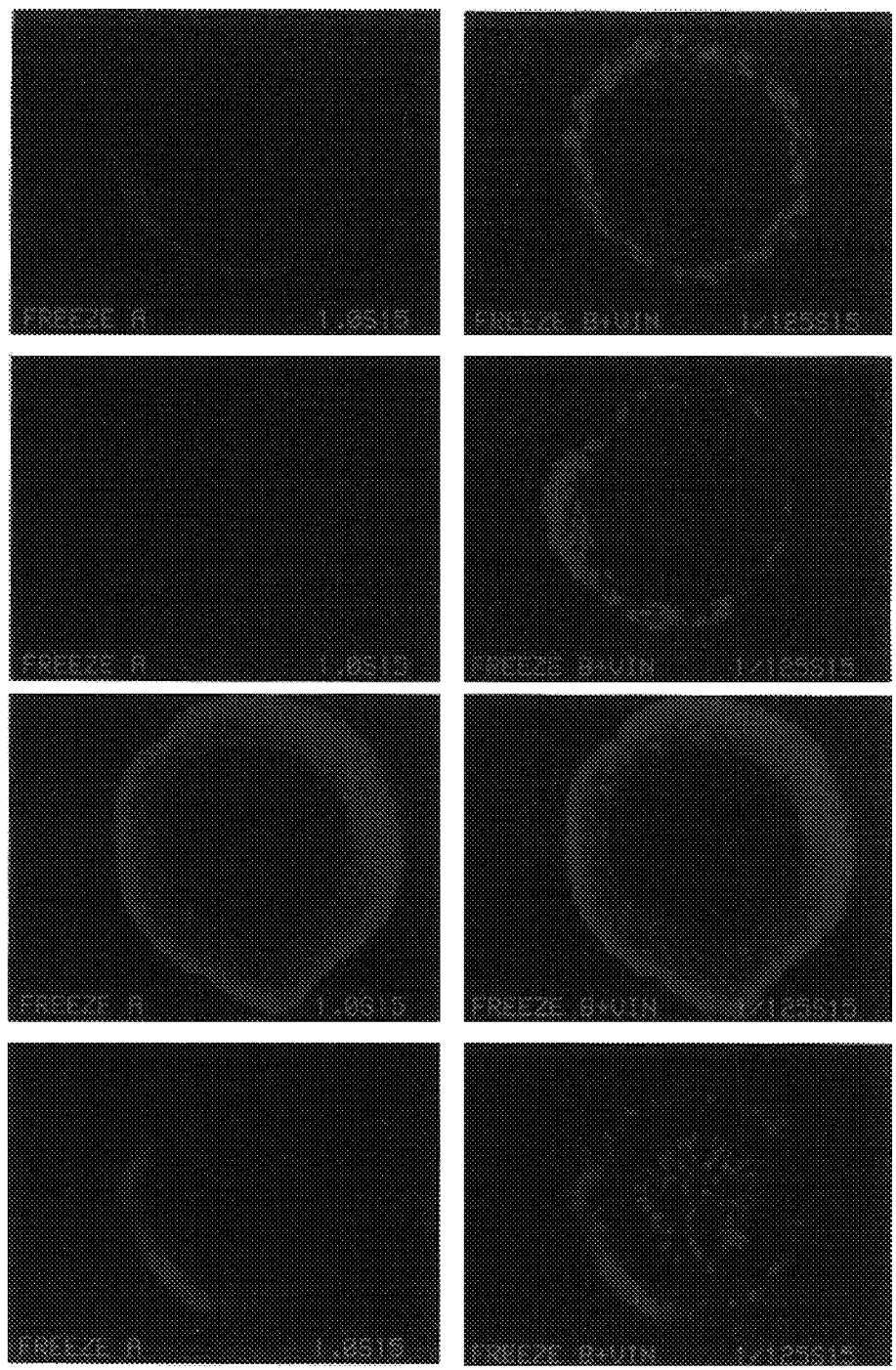
FIG. 4—Depicts transverse profile of hair follicle stained with antibodies.
Figure 5:
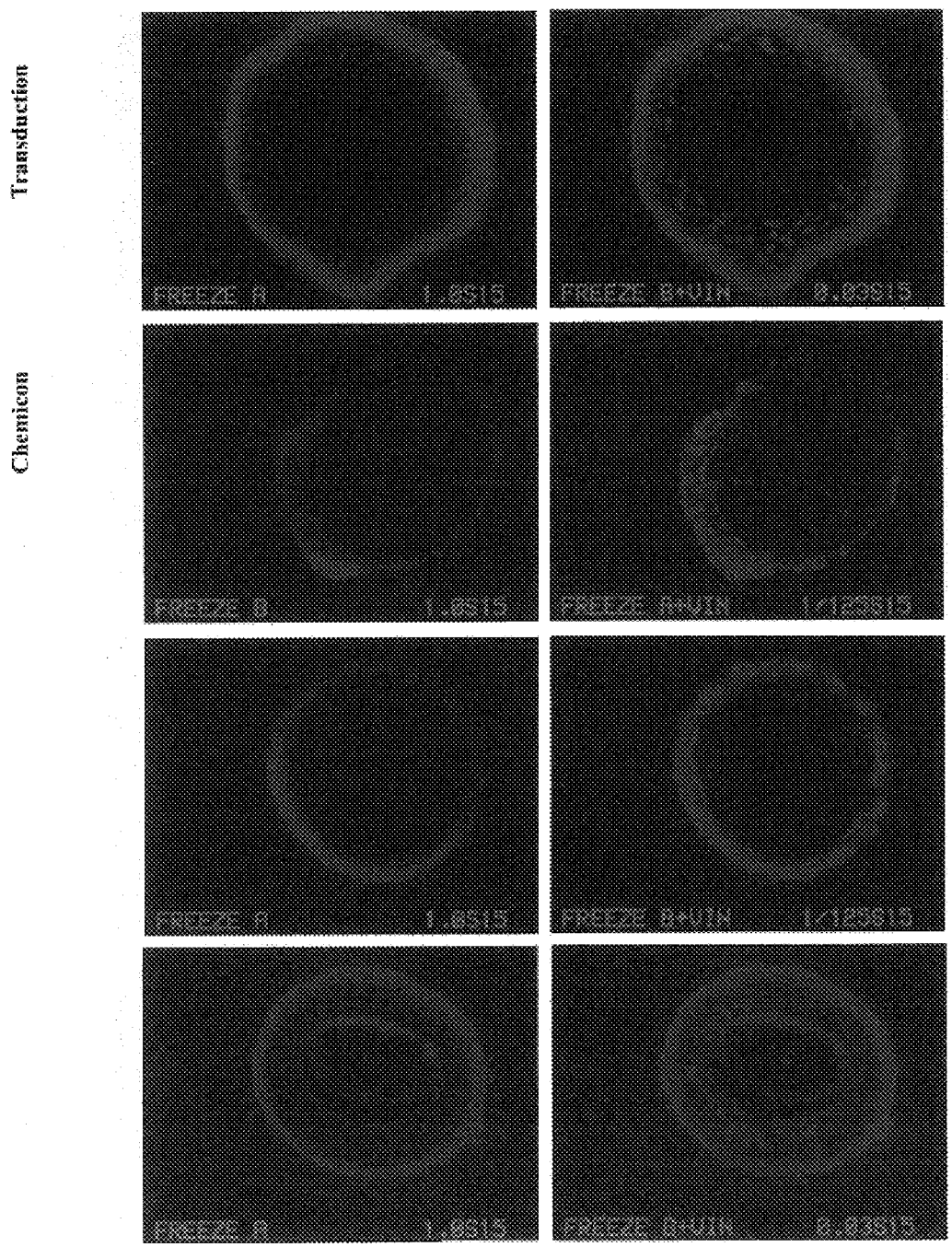
FIG. 5—Depicts transverse profile of hair follicle stained with anti-phosphorylated EGF-R antibody and Alexa594 anti-mouse Ig.

Anticancer treatment regimens generally involve invasive procedures such as biopsies to obtain tissue samples from patients to determine the progress and efficacy of treatment and to determine the next course of treatment. However, invasive biopsies subject the already immunocompromised patients to additional risks associated with anesthesia and secondary infections and may be not performed for the same reasons. Thus, valuable time is lost and the patient may be subject to unnecessary side effects from chemotherapies that may be ineffective in treating the cancer. The present invention provides non-invasive methods to determine cancer treatment effectiveness.

Several tumor cell types have been found to express much more growth factor receptors than normal cells and that these receptors are phosphorylated in cancers. For example, receptor protein tyrosine kinases such as the epidermal growth factor receptor (EGF-R) (Korc et al., 1993), c-erbB2 (Yamanaka et al., 1993), IGF-1 (Bergmann et al., 1995), and FGF-R (Wagner et al., 1998) are highly expressed in human pancreatic cancer tissues or pancreatic cancer cell lines. The present inventors have discovered that oral administration of the anticancer drug PKI166 to nude mice results in dramatic shrinkage of metastases of human cancer cells and a reduction in phosphorylated EGFR levels (see discussion below for details). The present invention takes advantage of this finding to provide a non-invasive method for determining the effectiveness of anticancer agents in treating tumors and metastases.

The inventors provide herein an assay that determines growth factor receptor phosphorylation in biological samples that can be obtained from subjects with out invasive procedures cells. Several cancer therapies, for example chemotherapeutic agents such as PKI166, inhibit growth factor receptor phosphorylation thereby mediating their therapeutic effectiveness. The present inventors have shown that such assays performed on samples obtained by non-invasive methods, such as hair follicles, buccal mucosa cells, pap-smear samples, bladder wash cells, skin scrapings and the like provide a determination of the efficacy of the anticancer therapy.

Therefore, obtaining a hair follicle and determining the phosphorylation of a growth factor receptor, such as the EGFR, prior to and after an anticancer treatment allows the analysis of the efficacy of the anticancer treatment. Thus, plucking a few hairs from a patient's head provides sample for the assay. This removes the need of the surgical procedure required for biopsies considerably reducing the associated risks of infection.

Thus, the present invention also provides cancer therapy regimens based on determining the effectiveness of one cancer therapy. For example, if one chemotherapeutic agent is ineffective, one may administer to a patient in need thereof another chamotherapeutic agent that targets other aspects of the cancer.

In one embodiments the invention teaches methods to detect the phosphorylation of growth factor receptors in hair follicles. This involves methods to prepare a hair follicle followed by immunostaining the hair follicle. The section entitled Examples details the methodology used.

Thus, according to the practice of certain specific embodiments of the invention, a sample of EGF-R expressing cells is collected from a patient suffering from a form of cancer which is known to overexpress EGF-R prior to any treatment with an anti-cancer agents, such as a protein kinase inhibitor. An example of such EGF-R expressing cells includes, but is not limited to, hair follicles, buccal mucosa, pap-smear samples, bladder wash cells, skin scrapings, etc. Such cells types can be easily collected through non-invasive means. The level of phosphorylation of EGF-R in the cells is determined for example, by any known methods of detecting growth factor receptor phosphorylation, such as using antibodies and is discussed in other parts of this specification. A preferred method of detection uses immunofluoresence. Shortly after the administration of the first dose of the anticancer therapy, a second sample of EGF-R expressing cells is obtained from the patient, the EGFR phosphorylation levels are determined again. Comparison of these levels provides the change in phosphorylation levels after the treatment which in turn determines the efficacy of the therapy.

I. Growth Factors and Receptors

Growth factors are proteins that bind to specific growth factor receptors on the cell surface, with the primary result of activating cellular proliferation and/or differentiation. Growth factor receptors are signaling proteins that transmit information regarding the binding of the growth factor to the interior of the cell which leads to activation of various signal transduction cascades in the cell. Many growth factor receptors are known. Some are quite versatile, stimulating cellular division in numerous different cell types; while others are specific to a particular cell-type.

For discussion purposes, the following description will focus on the epidermal growth factor receptor (EGFR). However, as will be known to the skilled artisan the methods of the present invention are applicable to all growth factor receptors that are elevated and/or have changed phosphorylation levels in cancer cells are contemplated. Some other exemplary growth factor receptors include fibroblast growth factor receptor, acidic fibroblast growth factor receptor, basic fibroblast growth factor receptor, insulin like growth factor receptor, nerve growth factor receptor, transforming growth factor α receptor, transforming growth factor β receptor, neuregulin/heregulin receptors, betacellulin receptors, amphiregulin receptors, heparin binding EGF-like growth factor receptors and the like. Changes in phosphorylation states of growth factors are seen in various cancers such as breast, prostrate, colon, pancreatic, head and neck, renal, bladder, blood, bone, bone marrow, brain, esophagus, gastrointestine, brain, kidney, liver, lung, nasopharynx, ovary, skin, stomach, uterine cancer and the like. The cancers may be pre-cancerous lesions, cancers, carcinomas, metastatic cancers and tumors. Furthermore the invention also contemplates all growth factor receptors expressed in hair follicles. Thus, the exemplary description below is not intended to limit the scope of the invention.

The epidermal growth factor (EGF), like all growth factors, binds to specific high-affinity, low-capacity receptors on the surface of responsive cells. Intrinsic to the EGF receptor is tyrosine kinase activity, which is activated in response to EGF binding. The kinase domain of the EGF receptor phosphorylates the EGF receptor itself (autophosphorylation) as well as other proteins, in signal transduction cascades, that associate with the receptor following activation.

EGF has proliferative effects on cells of both mesodermal and ectodermal origin, particularly keratinocytes and fibroblasts and exhibits negative growth effects on certain carcinomas as well as hair follicle cells. Growth-related responses to EGF include the induction of nuclear proto-oncogene expression, such as Fos, Jun and Myc. EGF also functions to decrease gastric acid secretion.

II. Detection of Growth Factor Receptor Phosphorylation

Phosphorylation assays are well known in the art. In general the assay is based on the phosphorylation of growth factor receptors upon binding to the growth factors. Typically binding of growth factors induce signal transduction cascades that activate a host of kinases that autophosphorylate the receptor especially at their tyrosine or serine-threonine residues depending on the receptor type.

Phosphorylation assays require the appropriate antibodies which comprise the anti-phosphorylated growth factor receptor antibodies, also referred to as the anti-activated growth factor receptor antibodies in some parts of this specification and are exemplified by anti-EGFR antibody, anti-IGFR antibody, anti-FGFR antibody and the like. In some embodiments, anti-phosphotyrosine or anti-phospho-serine or anti-phospho-threonine antibodies may be used as well.

The detection of a phosphorylated growth factor receptor comprises contacting a first antibody which is the anti-growth factor receptor antibody as described above with the cell or sample containing the phosphorylated growth factor receptor. This can be followed by contacting with a secondary antibody bound to a detectable label that can bind the first antibody. The secondary antibody is then detected by means of the detectable label.

The detectable label can be a fluor. The following fluors are specifically contemplated to be useful in practicing the present invention. Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red. Alternatively the label may be a enzymatic label or a radiolabel. The preferred detection method is by immunofluorescence.

Immunofluorescence microscopy is generally performed using a suitable objective on an epifluorescence microscope equipped with narrow bandpass excitation filters mounted in a filter wheel (Ludl Electronic Products, Hawthorne, N.Y.) to individually select for green, red, and blue fluorescence. Images are captured using a cooled CCD camera (Photometrics, Tucson, Ariz.) and SmartCapture software (Digital Scientific, Cambridge, England) on a computer. Images are further processed using Adobe Photoshop software (Adobe Systems, Mountain View, Calif.). One method for determining the immunofluorescent reaction intensity, is in terms of the optical density OD and can be measured using Optimas Image Analysis software.

III. Hair Follicle

Described in this section is the anatomy and life cycle of hair follicles. Hair follicle cross sections have been used to determine the levels of growth factor receptor phosphorylation in the present invention as the follicle cell is an growing epithelial cell and these cells reflect growth factor receptor levels seen in cancer cells. The present invention describes methods for immunostaining hair follicles with antibodies such as anti-phosphorylated growth factor receptor antibodies and anti-phosphotyrosine, anti-phosphoserine, anti-phosphothreonine antibodies.

The hair follicle is a tubular structure consisting of five concentric layers of epithelial cells. At the base, there is a bulbous expansion, the hair bulb, enclosing the dermal papilla (DP). As they are pushed towards the skin surface from the hair bulb, the inner three epithelial layers undergo keratinisation to form the fair shaft whilst the outer two layers form an epithelial sheath. At the hair bulb, all the layers merge to become indistinguishable from one another; the mass of cells destined to form the hair is known as the hair matrix.

During active hair growth, the epithelial cells surrounding the dermal papilla proliferate to form the four inner layers of the follicle whilst the outermost layer merely represents a downward continuation of the stratum germinativum of the surface epithelium. The whole epithelial mass surrounding the dermal papilla constitutes the hair root.

The cells of the innermost layer of the follicle undergo moderate keratinisation to form the medulla or core of the hair shaft; the medullary layer is often not distinguishable in fine hairs. The medulla is surrounded by a broad, highly keratinised layer, the cortex, which forms the bulk of the hair. The third cell layer of the follicle undergoes keratinisation to form a hard, thin cuticle on the surface of the hair. The cuticle consists of overlapping keratin plates, an arrangement which is said to prevent matting of the hair.

The fourth layer of the follicle constitutes the internal root sheath IRS; the cells of this layer become only lightly keratinised and disintegrate at the level of the sebaceous gland ducts leaving a space into which sebum is secreted around the maturing hair. The outermost layer, the external root sheath ERS, does not take part in hair formation; this layer is separated from the sheath of connective tissue CT surrounding the follicle by a thick, specialised basement membrane known as the glassy membrane GM.

In the growing follicle, large active melanocytes are scattered amongst the proliferating cells with melanin being incorporated in the cortex of the hair shaft. Black, brown and yellow forms of melanin are produced in various combinations to determine final hair color. In infancy, childhood and females, body hair is fine and soft and known as vellus in contrast to the coarser hair of the scalp which is known as terminal hair. Male sex hormone production at puberty is responsible for the development of further terminal public and axillary hair in both sexes and for the replacement of vellus hair with terminal hair on the mature male body.

The cross-sectional shape of hairs also varies between races. The straight hair of the Mongol races is round in cross-section, the wavy hair characteristics of Europeans is oval and the curly hair of black skinned people is more kidney-shaped.

In addition, the structure of hair follicles depends on the type of hair being produced. For example, the follicles of the scalp and other terminal hairs tend to be long and straight, whereas those of the body, which produce fine, downy hair (vellus), are relatively short and plump; curly hair may be produced by the curved follicles or follicles in which the hair bulb lies at an angle to the hair shaft.

Staining method permits clear delineation of the epithelial and collagenous elements of the hair follicle and are well known in the art. The dermal papilla DP is highly vascular and is separated from the epithelial cells by a basement membrane which is continuous with the glassy membrane G surrounding the follicle externally. The sheath of the follicle is also rich in blood vessels and contains a delicate plexus of sensory nerve endings which are receptive to minute movements of the hair follicle and thus act as highly sensitive touch receptors.

In hair cross sections one can find five cells layers of the hair follicle merging with the proliferating cells of the hair root. Large amount of pigment are seen in the basal layer extending up into the cortical layer and produced by melanocytes scattered along the basement membrane of the hair root.

Individual hair follicles undergo cycles of growth and quiescense and this is reflected in changes in their structure. In the growing phase, follicles penetrate deeply into the hypodermis and the hair bulb is prominent, whereas during the resting phase, follicles are shorter and the hair bulb is smaller lacking in a dermal papilla; quiescent follicles are known as club hairs.

The cyclical growth pattern is the factor which determines the limits of length reached by hairs in different parts of the body. For example, the growth phase of head hair is of the order of two years or more, each hair being shed during a follicular resting phase lasting a matter of months. Only a small portion of follicles are normally in the resting phase at any one time thus maintaining a continuous crop of hair. In contract, body hairs, eyebrows, eyelashes, etc., have a relatively short growth phase and longer resting phase preventing inappropriate overgrowth.

IV. Exemplary Anticancer Treatments

The following is a discussion on novel anticancer treatments developed previously by the current inventors. The mouse model and the combination therapy described herein are contemplated to be useful in the context of therapy for various cancers. Although this treatment was developed and performed for pancreatic cancer however it is contemplated that the treatment will be effective in other cancers that express phosphorylated growth factor receptors as well and thus the following is a description of this non limiting example.

Cancer of the exocrine pancreas is characterized by extensive local invasion and early lymphatic and hematogenous metastasis (Warshaw et al., 1992; Evans et al., 1997). At the time of diagnosis, more than 80% of patients present either locally advanced or metastatic disease (Warshaw et al., 1992; Evans et al., 1997; Wanebo and Vezeridis, 1996). The inability to detect pancreatic cancer at an early stage, its aggressiveness, and lack of effective systemic therapy are responsible for rapid death from this disease. In fact, only 1–4% of all patients with adenocarcinoma of the pancreas survive 5 years after diagnosis (Landis et al., 1999; Fernandez et al., 1994). For patients with advanced pancreatic cancer, even the recent introduction of the deoxycytidine analogue gemcitabine does not extend median survival beyond 6 months (Burris et al., 1997). Clearly, novel approaches to human pancreatic carcinoma therapy are needed.

Recent advances in the understanding of the biology of this disease may now offer new approaches to its therapy. Research efforts using archival human pancreatic tumor tissue or human pancreatic cancer cell lines have identified a number of characteristic biochemical and genetic abnormalities. These include point mutations at codon 12 of the K-ras oncogene in 75–90% of pancreatic adenocarcinoma specimens (Almoguera et al., 1988; Pellegata et al., 1994); homozygous deletions involving the cyclin-dependent (CDK)-inhibitory p16 gene, found in 85% of human pancreatic cancer xenografts (Caldas et al. 1994). Mutation or homozygous deletion of Smad4 (DPC4), a signal transduction molecule mediating the antiproliferative effects of tumor growth factor-beta (TGF-$\beta$) are found in over 50% of tumors (Hahn et al. 1996; Grau et al. 1997) as are mutations in p53 (Pellegata et al. 1994, Sinicrope et al. 1996). Other investigators have also demonstrated that receptor protein tyrosine kinases such as the epidermal growth factor receptor (EGF-R) (Korc et al. 1993), c-erbB2 (Yamanaka et al. 1993), IGF-1 (Bergmann et al. 1995), and FGF-R (Wagner et al. 1998) are highly expressed in human pancreatic cancer tissues or pancreatic cancer cell lines.

Extensive prior work has shown that cultured human pancreatic cancer cells express high levels of EGF-R and produce TGF-$\alpha$ and that human pancreatic cancers overexpress EGF-R and all 5 known ligands (Korc et al., 1993; Smith et al., 1987; Ebert et al., 1994; Kobrin et al., 1994). Furthermore, overexpression of EGF-R, TGF-$\alpha$, and EGF in human pancreatic tumors correlates with rapidly progressive disease when compared with tumors that fail to express the receptor and its ligands. Expression of a truncated EGF-R was associated with inhibition of pancreatic cancer cell growth and enhanced sensitivity to cisplatinum.

Though pancreatic cancer cells are characterized by the growth-promoting effects of genetic and biochemical changes, extensive interaction with normal host cells is necessary for progressive growth and metastasis of tumors. A critical tumor-host interaction necessary for local growth and metastasis is the neovascularization of growing tumors (Folkman, 1995; Hanahan and Folkman, 1996). The extent of angiogenesis depends on the balance between proangiogenic and antiangiogenic factors released by tumor cells and host cells.

Human pancreatic cancer cells secrete the proangiogenic molecules vascular endothelial growth factor (VEGF), interleukin-8 (IL-8), and basic fibroblast growth factor (bFGF) (Bruns et al., 1999; Kuniyasu et al., 1999). VEGF, currently regarded as the major proangiogenic factor for most types of human cancer, is strongly induced by EGF and TGF-$\alpha$. Thus, both EGF-R-mediated proliferation and angiogenesis are fundamental to the progressive growth of human pancreatic carcinoma and have been independently evaluated as targets for therapy. Ealuation of whether downregulation of EGF-R signaling pathways by a novel oral EGF-R tyrosine kinase inhibitor, PKI166, inhibits growth and metastasis of human pancreatic cancer implanted into the pancreas of nude mice showed that daily oral administration of PKI166 combined with weekly injections of gemcitabine lead to significant therapeutic effects mediated in part by induction of apoptosis in tumor-associated endothelial cells.

Blockade of the EGF-R signaling pathway by oral administration of the novel EGF-R tyrosine kinase inhibitor PKI166 combined with i.p. injections of gemcitabine significantly inhibited growth and lymph node and liver metastasis of human pancreatic carcinoma cells implanted into the pancreas of nude mice. Treatment with PKI166 alone or gemcitabine alone reduced the growth of the primary neoplasms by 45%. However, the combination of PKI166 and gemcitabine significantly decreased the growth of primary pancreatic cancers (by 85%) and the incidence (production) of lymph node and liver metastasis. Consequently, this combination therapy led to significant prolongation of survival, leaving some mice free of the disease. The daily oral administration of PKI166 (50 or 100 mg/kg body weight) was well tolerated. Immunohistochemical analyses of the pancreatic cancers demonstrated downregulation of activated EGF-R in lesions from mice treated with PKI166 alone or in combination with gemcitabine. This effect was accompanied by downregulation in production of the proangiogenic molecules VEGF and IL-8 and a significant decrease in microvessel density. Moreover, double staining of endothelial cells with antibodies against CD31 and TUNEL suggested that the reduction in microvessel density was due to a significant increase of apoptosis in the endothelial cells.

The progressive growth of human pancreatic cancer has been associated with expression of EGF-R (Korc et al., 1993; Ullrich et al., 1984) and coexpression of EGF-R with at least one of its ligands correlates with rapidly progressive disease. In addition to binding EGF and transforming growth factor-alpha (TGF-α), the EGF-R can be activated by heparin-binding EGF-like growth factor (HB-EGF), betacellulin, and amphiregulin. After ligand binding, EGF-R dimerizes and becomes activated through auto- and transphosphorylation on tyrosine residues within the intracellular domain. The EGF-R and its associated protein tyrosine kinases (PTK) also regulate apoptosis (Uckun et al., 1998a; Uckun et al., 1998b), and inactivation of EGF-R PTK has been shown to inhibit EGF-induced receptor autophosphorylation, MAPK activation, P13K activation, entry of cells into S phase, cyclin E-associated kinase activity, and consequently accumulation of cells in the G1 phase of the cell cycle (Mendelsohn, 1997). Targeting the EGF-R by an anti-EGF-R antibody (the Mendelsohn C225 antibody) in combination with radiation or chemotherapeutic agents can significantly inhibit the growth of human tumors in nude mice (Perrotte et al., 1999; Lipson et al., 1998; Ciardiello et al., 1996; Huang et al., 1999; Baselga et al., 1993; van Gog et al., 1998; Aboud-Pirak et al., 1988).

EGF-R is expressed not only on tumor cells (Korc et al., 1993; Smith et al., 1987; Ebert et al., 1994; Kobrin et al., 1994; Yamanaka et al., 1993; Wagner et al., 1996; Ullrich et al., 1984; Massague and Pandiella, 1993) but also on dividing endothelial cells (Goldman et al., 1993; Schreiber et al., 1986). Moreover, that activation of EGF-R on tumor cells has been shown to induce production of the proangiogenic molecule VEGF (Goldman et al., 1993). In mice treated with PKI166 alone or PKI166 plus gemcitabine, cells in pancreatic tumors expressed the EGF-R but not the activated (phosphorylated) EGF-R (Bruns et al., 2000). Treatment of mice with PKI166 alone or in combination with gemcitabine was associated with a decrease in tumor cell proliferation (PNCA) and an increase in apoptosis of tumor cells (TUNEL). Whether the increased apoptosis observed with the combination therapy was due to cellular arrest at the G1 restriction point, a consequence of EGF-R blockade (Ciardiello et al., 1996), was not established.

Immunohistochemical analyses of tumor specimens revealed that the treatment of mice with PKI166 and gemcitabine produced a significant decrease in the number of tumor-associated blood vessels in terms of the micro vessel density (MVD) (Bruns et al., 2000). This decrease could have been due to three nonexclusive mechanisms. First, endothelial cells within many neoplasms have been shown to express EGF-R (Goldman et al., 1993; Schreiber et al., 1986; Shiurba et al., 1988; Bohling et al., 1996; Rockwell et al., 1997). Moreover, the binding of TGF-α to EGF-R on endothelial cells has been shown to stimulate their proliferation (Goldman et al., 1993; Schreiber et al., 1986). Since blockade of the EGF-R results in cellular arrest at the G1 restriction point (Ullrich et al., 1984; Ciardiello et al., 1996), the decrease in MVD could have been due to a decrease in endothelial cell proliferation. Second, the immunohistochemical analyses of tumor specimens clearly shows that the decrease in activated EGF-R (in pancreatic tumors) was accompanied by a decrease in expression of the proangiogenic molecules VEGF and IL-8. Recent results have suggested that VEGF (Benjamin et al., 1999; Benjamin and Keshet, 1997) and IL-8 (Kumar et al., 1998; Kitadai et al., 1998; Xu et al., 1999) can act as survival factors for immature blood vessel endothelial cells and that VEGF can protect endothelial cells from apoptosis induced by TNF-α or other stimuli (Syridopoulos et al., 1997; Gerber et al., 1998; Nor et al., 1999; Watanabe and Dvorak, 1997).

Stimulation of the EGF-R signaling pathways is known to activate ras and raf, resulting in phosphorylation of c-fos and c-jun, leading to increased AP-1 transcriptional activity (Kerbel et al., 1998; Grugel et al., 1995; Rozakis-Adcock et al., 1993; Rak et al., 1995). Blockade of the EGF-R signaling pathways therefore results in reduced activity of AP-1 and, hence, reduced transcription of VEGF and IL-8. The decrease in VEGF production by tumor cells can prevent the recovery of dividing endothelial cells damaged by gemcitabine leading to the pronounced enhancement of apoptosis in tumor-associated endothelial cells. Third, PKI166 also inhibits the VEGF receptor KDR and Flt-1 activity (Table 2).

In summary, Bruns et al. (2000) shows that blockade of the EGF-R signaling pathway by the PTK inhibitor PKI166 in combination with gemcitabine produces significant therapy of human pancreatic carcinoma in nude mice. The inhibition of primary tumor growth and lymph node and liver metastasis is mediated by both direct antitumor effects and by antiangiogenesis effects. This combination therapy therefore provides a new approach to the treatment of various cancers.

V. Cancer Treatments

Several cancer therapies are known in the art and the use one or more of the various anticancer agents know will comprise in the context of this invention as a cancer treatment. An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing a tumor's size, inhibiting a tumor's growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents include, for example, chemotherapy agents (chemotherapy), radiotherapy agents (radiotherapy), a surgical procedure (surgery), immune therapy agents (immunotherapy), genetic therapy agents (gene therapy), hormonal therapy, other biological agents (biotherapy) and/or alternative therapies.

A. Chemotherapeutic Agents

The term "chemotherapy" refers to the use of drugs to treat cancer. A "chemotherapeutic agent" is used to connote a compound or composition that is administered in the treatment of cancer. Some examples of chemotherapeutic agents include antibiotic chemotherapeutics such as, Doxorubicin, Daunorubicin, Mitomycin (also known as mutamycin and/or mitomycin-C), Actinomycin D (Dactinomycin), Bleomycin, Plicomycin,. Plant alkaloids such as Taxol, Vincristine, Vinblastine. Miscellaneous agents such as Cisplatin, VP16, Tumor Necrosis Factor. Alkylating Agents such as, Carmustine, Melphalan (also known as alkeran, L-phenylalanine mustard, phenylalanine mustard, L-PAM, or L-sarcolysin, is a phenylalanine derivative of nitrogen mustard), Cyclophosphamide, Chlorambucil, Busulfan (also known as myleran), Lomustine. And other agents for example, Cisplatin (CDDP), Carboplatin, Procarbazine, Mechlorethamine, Camptothecin, Ifosfamide, Nitrosurea, Etoposide (VP16), Tamoxifen, Raloxifene, Estrogen Receptor Binding Agents, Gemcitabien, Navelbine, Farnesyl-protein transferase inhibitors, Transplatinum, 5-Fluorouracil, and Methotrexate, Temazolomide (an aqueous form of DTIC), or any analog or derivative variant of the foregoing. Table 1 lists numerous chemotherapeutics and their use in different cancer types.

Several chemotherapeutic agents change the phosphorylation state of growth factor receptors in cancer cells. For example the protein kinase inhibitor PKI166 decreases the amount of phosphorylated EGFR in cancer cells, which is indicative of tumor shrinkage and decrease of metastasis. Thus, protein kinase inhibitor drugs are another major class of chemotherapeutic compounds important in the context of the present invention.

TABLE 1

Chemotherapeutic Agents

| CLASS | AGENT | NONPROPRIETARY NAMES (OTHER NAMES) | DISEASE |
|---|---|---|---|
| Alkylating Agents | Nitrogen Mustards | Mechlorethamine (HN$_2$) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Melphalan (L-sarcolysin) | Multiple myeloma, breast, ovary |
| | | Chlorambucil | Chronic lymphocytic leukemia, primary macroglobulinemia, Hodgkin's disease, non-Hodgkin's lymphomas |
| | Ethylenimenes and Methylmelamines | Hexamethylmelamine | Ovary |
| | | Thiotepa | Bladder, breast, ovary |
| | Alkyl Sulfonates | Busulfan | Chronic granulocytic leukemia |
| | Nitrosoureas | Carmustine (BCNU) | Hodgkin's disease, non-Hodgkin's lymphomas, primary brain tumors, multiple myeloma, malignant melanoma |
| | | Lomustine (CCNU) | Hodgkin's disease, non-Hodgkin's lymphomas, primary brain tumors, small-cell lung |
| | | Semustine (methyl-CCNU) | Primary brain tumors, stomach, colon |
| | | Streptozocin (streptozotocin) | Malignant pancreatic insulinoma, malignant carcinoid |
| | Triazines | Dacarbazine (DTIC; dimethyltriazenoimidazole-carboxamide) | Malignant melanoma, Hodgkin's disease, soft-tissue sarcomas |
| Antimetabolites | Folic Acid Analogs | Methotrexate (amethopterin) | Acute lymphocytic leukemia, choriocarcinoma, mycosis fungoides, breast, head and neck, lung, osteogenic sarcoma |
| | Pyrimidine Analogs | Fluouracil (5-fluorouracil; 5-FU) Floxuridine (fluorode-oxyuridine; FUdR) | Breast, colon, stomach, pancreas, ovary, head and neck, urinary bladder, pre-malignant skin lesions (topical) |
| | | Cytarabine (cytosine arabinoside) | Acute granulocytic and acute lymphocytic leukemias |
| | Purine Analogs and Related Inhibitors | Mercaptopurine (6-mercaptopurine; 6-MP) | Acute lymphocytic, acute granulocytic and chronic granulocytic leukemias |
| | | Thioguanine (6-thioguanine; TG) | Acute granulocytic, acute lymphocytic and chronic granulocytic leukemias |
| | | Pentostatin (2-deoxycoformycin) | Hairy cell leukemia, mycosis fungoides, chronic lymphocytic leukemia |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | Epipodophyllotoxins | Etoposide Tertiposide | Testis, small-cell lung and other lung, breast, Hodgkin's disease, non-Hodgkin's lymphomas, acute granulocytic leukemia, Kaposi's sarcoma |
| | Antibiotics | Dactinomycin (actinomycin D) | Choriocarcinoma, Wilms' tumor, rhabdomyosarcoma, testis, Kaposi's sarcoma |
| | | Daunorubicin (daunomycin; rubidomycin) | Acute granulocytic and acute lymphocytic leukemias |
| | | Doxorubicin | Soft-tissue, osteogenic and other sarcomas; Hodgkin's disease, non-Hodgkin's |

TABLE 1-continued

Chemotherapeutic Agents

| CLASS | AGENT | NONPROPRIETARY NAMES (OTHER NAMES) | DISEASE |
|---|---|---|---|
| | | Bleomycin | lymphomas, acute leukemias, breast, genitourinary, thyroid, lung, stomach, neuroblastoma Testis, head and neck, skin, esophagus, lung and genitourinary tract; Hodgkin's disease, non-Hodgkin's lymphomas |
| | | Plicamycin (mithramycin) | Testis, malignant hypercalcemia |
| | | Mitomycin (mitomycin C) | Stomach, cervix, colon, breast, pancreas, bladder, head and neck |
| | Enzymes | L-Asparaginase | Acute lymphocytic leukemia |
| | Biological Response Modifiers | Interferon alfa | Hairy cell leukemia., Kaposi's sarcoma, melanoma, carcinoid, renal cell, ovary, bladder, non-Hodgkin's lymphomas, mycosis fungoides, multiple myeloma, chronic granulocytic leukemia |
| Miscellaneous Agents | Platinum Coordination Complexes | Cisplatin (cis-DDP) Carboplatin | Testis, ovary, bladder, head and neck, lung, thyroid, cervix, endometrium, neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essential thrombocytosis, malignant melanoma |
| | Methyl Hydrazine Derivative | Procarbazine (N-methylhydrazine, MIH) | Hodgkin's disease |
| | Adrenocortical Suppressant | Mitotane (o,p'-DDD) Aminoglutethimide | Adrenal cortex Breast |
| Hormones and Antagonists | Adrenocorticosteroids | Prednisone (several other equivalent preparations available) | Acute and chronic lymphocytic leukemias, non-Hodgkin's lymphomas, Hodgkin's disease, breast |
| | Progestins | Hydroxyprogesterone caproate Medroxyprogesterone acetate Megestrol acetate | Endometrium, breast |
| | Estrogens | Diethylstilbestrol Ethinyl estradiol (other preparations available) | Breast, prostate |
| | Antiestrogen | Tamoxifen | Breast |
| | Androgens | Testosterone propionate Fluoxymesterone (other preparations available) | Breast |
| | Antiandrogen | Flutamide | Prostate |
| | Gonadotropin-releasing hormone analog | Leuprolide | Prostate |

B. Radiotherapeutic Agents

Radiotherapeutic agents include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiations. It is most likely that all of these agents effect a broad range of damage DNA, on the precursors of DNA, the replication and repair of DNA, and the assembly and maintenance of chromosomes.

Radiotherapeutic agents and methods of administration, dosages, etc., are well known to those of skill in the art, and may be combined with the invention in light of the disclosures herein. For example, dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

C. Surgery

Approximately 60% of persons with cancer will undergo surgery of some type, which includes, for example, preventative, diagnostic or staging, curative and palliative surgery. Surgery, and in particular a curative surgery, may be used in conjunction with other therapies, such as the present invention and one or more other agents.

Curative surgery includes resection in which all or part of cancerous tissue is physically removed, excised and/or destroyed. It is further contemplated that surgery may remove, excise or destroy superficial cancers, precancers, or incidental amounts of normal tissue. Treatment by surgery includes for example, tumor resection, laser surgery, cryosurgery, electrosurgery, and miscopically controlled surgery (Mohs' surgery). Tumor resection refers to physical removal of at least part of a tumor. Upon excision of part of all of cancerous cells, tissue, or tumor, a cavity may be formed in the body.

D. Immunotherapeutic Agents

An immunotherapeutic agent generally relies on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (e.g., a chemotherapeutic, a radionuclide, a ricin A chain, a cholera toxin, a pertussis toxin, etc.) and serve merely as a targeting agent. Such antibody conjugates are called immunotoxins, and are well known in the art (see U.S. Pat. Nos. 5,686,072, 5,578,706, 4,792,447, 5,045,451, 4,664,911, and U.S. Pat. No. 5,767,072, each incorporated herein by reference). Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

E. Genetic Therapy Agents

A tumor cell resistance to agents, such as chemotherapeutic and radiotherapeutic agents, represents a major problem in clinical oncology. Improvement of the efficacy of one or more anti-cancer agents is possible by combining such an agent with gene therapy. For example, the herpes simplex-thymidine kinase (HS-tK) gene, when delivered to brain tumors by a retroviral vector system, successfully induced susceptibility to the antiviral agent ganciclovir (Culver, et al., 1992). Gene therapy agents could encode proteins or antisense molecules that change growth factor receptor phosphorylation, for example genes encoding growth factors. In the context of the present invention, it is contemplated that gene therapy could be used similarly alone or in conjunction with other anticancer agents and one may determine the efficacy of such a treatment using methods of the present invention.

F. Combination Anticancer Therapies

A variety of cancer therapies such as those described above may be used in context of the present invention. Generally, in order to increase the effectiveness of the cancer therapy, it may be desirable to combine two or more anticancer agents.

Administration of one anticancer agent may precede or follow the other anticancer agent by intervals ranging from minutes to days to weeks. In embodiments where both anticancer agents are administered together, one would generally ensure that a significant period of time did not expire between the time of each delivery. In such instances, it is contemplated that one would administer to a patient both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either agent will be required to achieve complete cancer cure. Various combinations may be employed, where the one anticancer agent is "A" and another is "B", as exemplified below:

A/B/A B/A/B B/B/A A/A/B B/A/A A/B/B B/B/B/A B/B/ A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations also are contemplated an the assay of improvement or reduction of phosphorylation state of the growth factor receptor as described in the present invention can be performed at any stage during these combination treatments to determine the efficacy of the treatment and to readjust the administration of drugs as required.

VI. Antibodies

In certain aspects of the invention, one or more antibodies are used to detect the phosphorylated growth factor receptors on the surface of cells as a means of determining the efficacy of a cancer treatment and further as a means for developing a better cancer therapy regimen. These antibodies may be obtained commercially or produced and find use in various diagnostic and therapeutic applications, described herein.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

However, "humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's dental disease are likewise known and such custom-tailored antibodies are also contemplated.

The methods for generating monoclonal antibodies (MAbs) generally begin along the same lines as those for preparing polyclonal antibodies. Briefly, a polyclonal antibody is prepared by immunizing an animal with a LEE or CEE composition in accordance with the present invention and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia, synthetic compositions or LEEs or CEEs encoding such adjuvants.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m$^2$) (Johnson/Mead, N.J.), cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen including but not limited to subcutaneous, intramuscular, intradermal, intraepidermal, intravenous and intraperitoneal. The production of polyclonal antibodies may be monitored by sampling blood of the immunized animal at various points following immunization.

A second, booster dose (e.g., provided in an injection), may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60–61), but mice are preferred, with the BALB/c mouse being most preferred as this is most routinely used and generally gives a higher percentage of stable fusions.

The animals are injected with antigen, generally as described above. The antigen may be mixed with adjuvant, such as Freund's complete or incomplete adjuvant. Booster administrations with the same antigen or DNA encoding the antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). cites). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729–6 are all useful in connection with human cell fusions.

One murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies. In another example, LEEs or CEEs can be used to produce antigens in vitro with a cell free system. These can be used as targets for scanning single chain antibody libraries. This would enable many different antibodies to be identified very quickly without the use of animals.

Alternatively, monoclonal antibody fragments encompassed by the present invention can be synthesized using an automated peptide synthesizer, or by expression of full-length gene or of gene fragments in E, coli.

A. Antibody Conjugates

The present invention further provides antibodies to phosphorylated growth factor receptors and agents may be linked to the antibody to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or poly-nucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin. In context of this invention it is contemplated that receptor molecules will be used.

Any antibody of sufficient selectivity, specificity or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al, 1988), and contains epitopes (idiotopes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired.

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody-directed imaging".

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such as diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

B. Immunodetection Methods

In still further embodiments, the present invention concerns immunodetection methods for binding, purifying, removing, quantifying and/or otherwise generally detecting biological components such as growth factor receptors especially in their phosphorylated state. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle M H and Ben-Zeev O, 1999; Gulbis B and Galand P, 1993; De Jager R et al., 1993; and Nakamura et al., 1987, each incorporated herein by reference.

In general, the immunobinding methods include obtaining a sample suspected of containing growth factor receptors especially in their phosphorylated state, and contacting the sample with a first and/or second phosphorylated growth factor receptor antibody, as the case may be, under conditions effective to allow the formation of immunocomplexes.

These methods include methods for purifying a growth factor receptor especially in its phosphorylated state. In these instances, the antibody removes the antigenic phosphorylated growth factor receptors component from a sample. The antibody will preferably be linked to a solid support, such as in the form of a column matrix, and the sample suspected of containing the phosphorylated anti-growth factor receptor antigenic component will be applied to the immobilized antibody. The unwanted components will be washed from the column, leaving the antigen immunocomplexed to the immobilized antibody to be eluted.

The immunobinding methods also include methods for detecting and quantifying the amount of an antigen component in a sample and the detection and quantification of any immune complexes formed during the binding process. Here, one would obtain a sample suspected of containing an antigen, and contact the sample with an antibody against the phosphorylated growth factor receptor produced antigen, and then detect and quantify the amount of immune complexes formed under the specific conditions.

In terms of antigen detection, the biological sample analyzed may be any sample that is suspected of containing an antigen, such as, for example, a tissue section or specimen, a homogenized tissue extract, a cell, an organelle, separated and/or purified forms of any of the above antigen-containing compositions, or even any biological fluid that comes into contact with the cell or tissue, including blood and/or serum, although tissue samples or extracts are preferred.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any phosphorylated anti-growth factor receptor antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The phosphorylated anti-growth factor receptor antigen antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/ antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

The immunodetection methods of the present invention have evident utility in the diagnosis and prognosis of conditions such as various cancers wherein a specific phosphorylated growth factor receptor is overexpressed, such as EGF-R in pancreatic cancer, heregulins in breast cancer, etc. Here, a biological and/or clinical sample suspected of containing a specific cancer associated with altered phosphorylated growth factor receptor is used. However, these embodiments also have applications to non-clinical samples, such as in the titering of antigen or antibody samples, for example in the selection of hybridomas.

In the clinical diagnosis and/or monitoring of patients with various forms a disease, such as, for example, cancer, the detection of a cancer specific phosphorylated growth factor receptor, and/or an alteration in the levels of a cancer specific gene product, in comparison to the levels in a corresponding biological sample from a normal subject is indicative of a patient with cancer. However, as is known to those of skill in the art, such a clinical diagnosis would not necessarily be made on the basis of this method in isolation.

Those of skill in the art are very familiar with differentiating between significant differences in types and/or amounts of biomarkers, which represent a positive identification, and/or low level and/or background changes of biomarkers. Indeed, background expression levels are often used to form a "cut-off" above which increased detection will be scored as significant and/or positive. Of course, the antibodies of the present invention in any immunodetection or therapy known to one of ordinary skill in the art.

(i) ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, or Western blotting, dot blotting, FACS analyses, and the like may also be used.

In one exemplary ELISA, the anti-phosphorylated growth factor receptor antibody as described in the invention are immobilized onto a selected surface exhibiting protein affinity, such as a well in a polystyrene microtiter plate. Then, a test composition suspected of containing the antigen, such as a clinical sample, is added to the wells. After binding and/or washing to remove non-specifically bound immune complexes, the bound antigen may be detected. Detection is generally achieved by the addition of another anti-phosphorylated growth factor receptors is linked to a detectable label. This type of ELISA is a simple "sandwich ELISA". Detection may also be achieved by the addition of a second anti-phosphorylated growth factor receptors antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with the anti-phosphorylated growth factor receptor antibody. After binding and/or washing to remove non-specifically bound immune complexes, the bound anti-phosphorylated growth factor receptor antibodies are detected. Where the initial anti-phosphorylated growth factor receptor antibodies are linked to a detectable label, the immune complexes may be detected directly. Again, the immune complexes may be detected using a second antibody that has binding affinity for the first anti-phosphorylated growth factor receptors antibody, with the second antibody being linked to a detectable label.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label.

Quantification is then achieved by measuring the degree of color generated, e.g., using a visible spectra spectrophotometer.

(ii) Immunohistochemistry

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25–50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

(iii) Kits

In further embodiments, the invention provides kits for use in detecting the efficacy of anticancer treatments, e.g., in biological samples obtained by non invasive means. Such kits will generally comprise one or more antibodies that have immunospecificity for the phosphorylated growth factor receptors identified in the present invention.

The kits will thus comprise, in suitable container means, (a) components for extracting samples by non-invasive means before and after administration of an anticancer agent; (b) components for determining phosphorylation states of growth factor receptors in the samples.

Kits comprising antibodies, such as anti-phosphorylated growth factor antibody, anti-phosphotyrosine antibody, an anti-phosphoserine antibody or and anti-phosphothreonine antibody, will be preferred in many cases. In more preferred embodiments, it is contemplated that the antibodies will be those that bind to the phosphorylated growth factor antibody. Monoclonal antibodies are readily prepared and will often be preferred. Where cancer marker proteins or peptides are provided, it is generally preferred that they be highly purified.

The immunodetection reagents of the kit may take any one of a variety of forms, including those detectable labels that are associated with, or linked to, the given antibody or antigen itself. Detectable labels that are associated with or attached to a secondary binding ligand are also contemplated. Exemplary secondary ligands are those secondary antibodies that have binding affinity for the first antibody or antigen.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Assay of Hair Follicle Cells

Hair follicle cells obtained from patients prior to and after treatment with an anticancer drug were processed for the determination of growth factor receptor phosphorylation as follows. Hair follicles were fixed in acetone for 10 minutes, embedded in OCT and frozen in liquid nitrogen. Frozen sections were cut and incubated with the anti-phosphorylated EGF-R antibody (Chemicon) followed by Alexa goat anti-mouse IgG antibody (Molecular Probes) and examined in a fluorescence microscope. Samples fixed in acetone and stored in the refrigerator for a week were also used in some cases.

The hair follicles were dissected under a dissecting microscope and the hair shaft just above the follicle was cut. The follicles were transferred to an 8-chambered slide (Lab-Tek, Fisher Scientific) filled with a protein blocking solution containing 4% fish gelatin in PBS. After minutes excess solution was removed and the follicles were incubated with a 1:50 dilution of anti-activated EGF-R, diluted in protein blocking solution overnight at 4° C. The samples were washed 3×3 minutes followed by incubation with the protein blocking solution for 10 minutes. The samples were then incubated with Alexa 594 conjugated goat anti-mouse IgG for 1 hr at room temp and rinsed well. The follicles were transferred with fine forceps to hanging drop slides previously filled with Vectashield mounting medium containing DAPI (Vector Laboratories Inc., Burlingame Calif.). Samples were mounted in hanging drop slides to prevent crushing of the hair follicles and examined in a Zeiss Axioplan fluorescence microscope. FIGS. 1–5 depict the immunofluorescent hair follicles stained for phosphorylated EGF-R.

Figure 6:
FIG. 6—Backscatter scanning electron microscopy sections of hair follicles incubated with anti-phosphorylated EGF-R followed by gold-labeled anti-mouse IgG enhanced with Goldenhance.
Figure 7:
FIG. 7—Backscatter scanning electron microscopy sections of hair follicles at a higher magnification than in FIG. 6 depicting higher concentrations of gold particles in the outer root sheath as compared to the inner root sheath.

The staining was further verified by Electron Microscopy. The frozen hair follicles were incubated with anti-activated EGF-R as above and followed by incubation with gold-labeled anti-mouse IgG (Ted Pella Inc., CA). The gold particles were enhanced with Golgenhance (Nanoprobes, NY). The sections were processed for backscatter scanning electron microscopy. Appropriate controls were performed. FIG. 6 depicts a low magnification of a tangential section of the hair follicle and the area in the box is shown at a higher magnification in FIG. 7. Clearly the gold particles are more concentrated in the outer root sheath than in the inner root sheath of the hair follicle.

The inventors also contemplate that the role of the hair cell cycle plays a role in expression of the growth factor receptors and cytokine receptors. They envision that this will require PCNA/TUNEL ratio to determine the different stages in hair cycle.

EXAMPLE 2

EGF-R Phosphorylation in Tumor Cells Treated with PKI166

Materials And Methods

Pancreatic Cancer Cell Lines and Culture Conditions. For these studies, highly metastatic cell line (L3.6pl) isolated after successive cycles of selections in nude mice (Bruns et al. 1999) was used. The original COLO 357 human pancreatic cancer cell line established from a celiac lymph node metastasis of well differentiated, mucin-containing pancreatic cancer cells (Morgan et al. 1980) was injected by Vezeridis et al. into the spleen of nude mice to isolate liver metastases designated as the L3.3 line (Vezeridis et al. 1992). The L3.3 cells were injected into the pancreas of nude mice and isolated liver metastases which are designated as L3.4pl (pancreas-liver). After two additional orthotopic injection-selection cycles, the cells designated as L3.6pl were isolated which produced spontaneous liver metastasis at a significantly higher incidence than the original COLO 375 cells (Bruns et al. 1999). The highly metastatic human pancreatic cancer L3.6pl cells were maintained in Dulbecco's minimal essential medium (DMEM), supplemented with 5% fetal bovine serum (FBS), sodium pyruvate, nonessential amino acids, L-glutamine, a two-fold vitamin solution (Life Technologies, Inc., Grand Island, N.Y.), and penicillin-streptomycin-mixture (Flow Laboratories, Rockville, Md.). Adherent monolayer cultures were maintained on plastic and incubated at 37° C. in a mixture of 5% $CO_2$ and 95% air. The cultures were free of Mycoplasma and the following pathogenic murine viruses: reovirus type 3, pneumonia virus, K virus, Theiler's encephalitis virus, Sendai virus, minute virus, mouse adenovirus, mouse hepatitis virus, lymphocytic choriomeningitis virus, ectromelia virus, and lactate dehydrogenase virus (assayed by M.A. Bioproducts, Walkersville, Md.). The cultures were maintained for no longer than 12 wk after recovery from frozen stocks.

Reagents. PKI166 (4-(R)-phenethylamino-6-(hydroxyl) phenyl-7H-pyrrolo[2.3-d]-pyrimidine), a novel EGF-R tyrosine kinase inhibitor, was synthesized and provided by Novartis Pharma AG (Basle, Switzerland). For in vivo administration, PKI166 was dissolved in DMSO/0.5% Tween 80 and then diluted 1:20 in Hanks' balanced salt solution (HBSS) (Traxler et al 1999). All antibodies were purchased as listed: rabbit anti-VEGF/VPF (Santa Cruz, Santa Cruz, Calif.), polyclonal rabbit anti-human IL-8 (Biosource International, Camarillo, Calif.), rat anti-mouse CD31/PECAM-1 and peroxidase-conjugated rat anti-mouse IgG1 (Pharmingen, San Diego, Calif.), mouse anti-PCNA clone PC 10 (DAKO A/S, Denmark), rat anti-mouse macrophage scavenger receptor (Serotec, Raleigh, N.C.), mouse anti-human EGF-R (activated form) IgG1 (Chemicon, Temecula, Calif.), monoclonal mouse anti-human IgG1 EGF-R clone 30 (Biogenex, San Ramon, Calif.), peroxidase-conjugated $F(ab')_2$ goat anti-rabbit IgG $F(ab')_2$, peroxidase-conjugated goat anti-mouse IgG $F(ab)_2$ fragment, affinipure Fab-fragment goat anti-mouse IgG, peroxidase-conjugated goat anti-rat IgG, and Texas Red-conjugated goat anti-rat IgG (Jackson Research Laboratories, West Grove, Calif.), peroxidase-conjugated rat anti-mouse IgG2a (Serotec, Harlan Bioproducts for Science, Inc., Indianapolis, Ind.), monoclonal anti-phosphotyrosine MAb 4G10 and polyclonal sheep anti-human EGF-R (Upstate Biotechnology, Lake Placid, N.Y.), MAb anti-EGF-R (clone EGF-RI) (Amersham Life Science, Inc., Arlington Heights, Ill.) for immunoprecipitation and human IgG (Sigma Immunochemicals, St. Louis, Mo.), Hoechst dye 3342 MW 615.9 (Hoechst, Warrington, Pa.), stable 3,3'-diaminobenzidine (DAB) (Research Genetics, Huntsville, Ala.), 3-amino-9-ethylcarbazole (AEC) (Biogenex Laboratories, San Ramon, Calif.), and Gill's hematoxylin (Sigma Chemical Co., St. Louis, Mo.). Osmium tetraoxide (4% aqueous solution) was purchased from Electron Microscopy Sciences (Fort Washington, Pa.), prolong solution from Molecular Probes (Eugene, Oreg.), and pepsin from Biomeda (Foster City, Calif.).

Tetrazolium (MTT, M2128) was purchased from Sigma Chemical Co. and a stock solution was prepared by dissolving 5 mg of MTT in 1 ml PBS and filtering the solution to remove particulates. The solution was protected from light, stored at 4° C., and used within a month. The ECL detection system was purchased from Amersham, Inc. (Arlington Heights, Ill.), and the VEGF and IL-8 ELISA kits from R&D Systems, Inc. (Minneapolis, Minn.). TUNEL was performed using a commercial apoptosis detection kit (Promega, Madison, Wis.) with modifications. [$\alpha$-$^{32}$P] was purchased from Amersham Corp.

Preparation of Enzymes and Kinase Assays. In vitro enzyme assays using EGF-R (McGlynn et al. 1992a), Abl (Geissler et al. 1992), and c-Src (Geissler et al. 1990) protein tyrosine kinases were performed in 96-well plates as a filter binding assay. Briefly, EGF-R intracellular kinase domain (EGF-R-ICD) was assayed in 20 mM Tris-HCl, pH 7.5, 10 mM $MnCl_2$, 10 µM $Na_3VO_4$, 1 mM DTT, 0.1 µCi/assay [$\gamma$-$^{33}$P]ATP, 0.4 µM ATP, 2 µ/ml poly(Glu,Tyr 4:1) (Sigma P275), 1% DMSO, and 30 ng EGF-R-ICD in a total volume of 30 µl. The His-tagged kinase domain of c-Abl was cloned and expressed in the baculovirus/Sf9 system as described previously (Bhat et al. 1997) and assayed in 20 mM Tris-HCl, pH 7.5, 10 mM $MgCl_2$, 10 µM $Na_3VO_4$, 1 mM DTT, 0.06 µCi/assay (=30 µl ) [$\gamma$-$^{32}$P]ATP, 5 µM ATP, 30 µg/ml poly(Ala,Glu,Lys,Tyr 6:2:5:1) (Sigma P1152), 1% DMSO, and 50 ng c-Abl enzyme. Src kinase (60 µg/ml) was preactivated with 50 µM ATP for 10 min at room temperature, and kinase inhibition was measured in 20 mM Tris-HCl, pH 7.5, 10 mM $MgCl_2$, 10 µM $Na_3VO_4$, 1 mM DTT, 0.1 µCi/assay (=30 µl ) [$\gamma$-$^{33}$P]ATP, 20 µM ATP, 25 µg/ml poly(Glu,Tyr 4:1), 1% DMSO, and 10 ng c-Src enzyme.

GST-fused kinase domains of Kdr, Flt-1, Flk, Tek, c-Met, and c-Kit were expressed in baculovirus and purified over glutathione-Sepharose. Kinase inhibition was measured by detecting the decrease in phosphorylation of poly(Glu,Tyr 4:1) essentially as previously described for EGF-R. Each kinase was incubated under optimized buffer conditions in 20 mM Tris-HCl, pH 7.5, 1–3 mM $MnCl_2$, 3–10 mM $MgCl_2$, 10 µM $Na_3VO_4$, 1 mM DTT, 0.2 µCi/[$\gamma$-$^{33}$P]ATP, 1–8 µM ATP, 3–8 µg/ml poly(Glu,Tyr 4:1), 1% DMSO in a total volume of 30 µl in the presence or absence of PKI166 for 10 min at ambient temperature. Reactions were terminated by adding 10 µl of 250 mM EDTA, and the reaction mixture was transferred onto an Immobilon-PVDG membrane (Millipore, Bedford, Mass.). Following a washing (0.5% $H_3PO_4$), a soaking in EtOH, and drying, filters were counted in a liquid scintillation counter. $IC_{50}$ values for PKI166 were calculated by linear regression analysis of the percentage inhibition. Inhibition of Cdc2/cyclin B protein kinase (Arion et al. 1988; Partanen et al. 1991) and PKC (McGlynn et al. 1992b) was assayed as previously described.

Animals and Orthotopic Implantation of Tumor Cells. Male athymic nude mice (NCr-nu) were purchased from the Animal Production Area of the National Cancer Institute-Frederick Cancer Research and Development Center (Frederick, Md.). The mice were housed and maintained in laminar flow cabinets under specific pathogen-free conditions in facilities approved by the American Association for Accreditation of Laboratory Animal Care and in accordance with current regulations and standards of the U. S. Department of Agriculture, U.S. Department of Health and Human Services, and the National Institutes of Health. The mice were used in accordance with institutional guidelines when they were 8 to 12 wk old.

Orthotopic Implantation of Tumor Cells. To produce tumors, L3.6pl cells were harvested from subconfluent cultures by a brief exposure to 0.25% trypsin and 0.02% EDTA. Trypsinization was stopped with medium containing 10% FBS, and the cells were washed once in serum-free medium and resuspended in HBSS. Only suspensions consisting of single cells with greater than 90% viability were used for the injections. Cells were injected into the pancreas as described previously. The mice were killed when moribund (5–6 wk). The size and weight of the primary pancreatic tumors, the incidence of regional (celiac and paraaortal) lymph node metastasis, and the number of liver metastases were recorded. Histopathology confirmed the nature of the disease. For immunohistochemistry and histology staining procedures, one part of the tumor tissue was fixed in formalin and embedded in paraffin. Another part of the tumor was embedded in OCT compound (Miles Inc, Elkhart, Ind.), snap-frozen in liquid nitrogen, and stored at −70° C.

Therapy of Established Human Pancreatic Carcinoma Tumors Growing in the Pancreas of Athymic Nude Mice. Seven days after implantation of tumor cells into the pancreas, 5 mice were killed and the presence of tumor lesions was determined. At this time, the median tumor volume was 18 $mm^3$. Histological examination confirmed the lesions to be actively growing pancreatic cancer. The mice were randomized into the following treatment groups (n=10): daily oral administration of PKI166 (100 mg/kg), twice-a-week i.p. injections of gemcitabine at 125 mg/kg, 10 daily oral administrations of PKI166 (50 or 100 mg/kg), and twice-a-week i.p. injections of gemcitabine (125 mg/kg). Control mice received oral vehicle solution for PKI166 (DMSO/ 0.5% Tween 80 diluted 1:20 in HBSS), and i.p. HBSS.

The therapy experiment was repeated to determine overall survival. To do so, mice were implanted with L3.6pl cells in the pancreas and randomized to the four treatment groups (n=5) on day 7. The mice were killed and necropsied when they became moribund. The volume of pancreatic tumors and the incidence of lymph node and liver metastasis was recorded. Survival was evaluated by the Kaplan-Meier method.

To evaluate the therapeutic effect of gemcitabine in this animal model, a preliminary dose-response experiment was performed. Tumor cells (L3.6pl) were injected into the pancreas, and 7 days later, groups of mice (n=5) received twice weekly i.p. injections of 500, 250, 125, 62, 31, 15.5, and 7.5 mg/kg gemcitabine. All mice were killed on day 35. The volume of tumors and incidence of metastasis were determined.

Necropsy Procedures and Histological Studies. Mice were euthanized and the body weight was determined. Primary tumors in the pancreas were excised and weighed. For immunohistochemistry and H&E staining procedures, one part of the tumor tissue was formalin-fixed and paraffin-embedded and another part was embedded in OCT compound (Miles, Inc, Elkhart, Ind.), rapidly frozen in liquid nitrogen, and stored at −70° C. Visible liver metastases were counted with the aid of a dissecting microscope and processed for H&E staining. All macroscopically enlarged regional (celiac and paraaortal) lymph nodes were harvested, and the presence of metastatic disease was confirmed by histology.

Immunohistochemical (IHC) Determination of VEGF, IL-8, PCNA, CD31/PECAM-1, and EGF-R. Paraffin-embedded tissues were used for identification of VEGF, IL-8, EGF-R, and proliferating cell nuclear antigen (PCNA). Sections (4–6 μm thick) were mounted on positively-charged Superfrost slides (Fisher Scientific, Co., Houston, Tex.) and dried overnight. Sections were deparaffinized in xylene followed by treatment with a graded series of alcohol (100%, 95%, 80% ethanol/dd$H_2$O [v/v]) and rehydrated in PBS, pH 7.5. Sections analyzed for PCNA were microwaved 5 min for "antigen retrieval" (Shi et al. 1991). All other paraffin-embedded tissues were treated with pepsin (Biomeda) for 15 min at 37° C. and washed with PBS. Frozen tissues used for identification of CD31/PECAM-1, and activated EGF-R were sectioned (8–10 μm), mounted on positively charged Plus slides (Fisher Scientific), and air-dried for 30 min. Frozen sections were fixed in cold acetone (5 min), acetone/chloroform (v/v) (5 min), and acetone (5 min) and washed with PBS. Immunohistochemical procedures were performed as described previously (Rak et al. 1996). Positive reaction was visualized by incubating the slides with stable 3,3'-diaminobenzidine (DAB) for 10–20 min or 3-amino-9-ethylcarbazole (AEC) after CD31 staining. The sections were rinsed with distilled water, counterstained with Gill's hematoxylin for 1 min, and mounted with Universal Mount (Research Genetics). Control samples exposed to secondary antibody alone showed no specific staining. Sections analyzed for activated EGF-R were pretreated with goat anti-mouse IgG F(ab)$_2$ fragment (1:10 dilution in PBS) for 4–6 h before incubation with the primary antibody. The positive reaction following staining for activated EGF-R was enhanced with osmium tetraoxide (4% aqueous solution) at a 1:1000 dilution in dd$H_2$O after incubation with DAB.

Immunofluorescence Double Staining for CD31/PECAM-1 (Endothelial Cells) and TUNEL (Apoptotic Cells). Frozen tissues were sectioned (8–10 μm), mounted on positively charged slides, air-dried for 30 min, and fixed in cold acetone for 5 min, acetone+chloroform (1:1) for 5 min, and acetone for 5 min. Samples were washed 3 times with PBS, incubated with protein-blocking solution containing 5% normal horse serum and 1% normal goat serum in PBS for 20 min at room temperature, and incubated with the appropriate dilution (1:400) of rat monoclonal anti-mouse CD31 antibody (human cross-reactive) over 18 h at 4° C. After the samples were rinsed 4 times for 3 min each with PBS, the slides were incubated with the appropriate dilution (1:200) of secondary goat anti-rat conjugated to Texas Red for 1 h at room temperature in the dark. Samples were washed twice with PBS containing 0.1% Brij and washed with PBS for 5 min.

TUNEL was performed using a commercially available apoptosis detection kit with the following modifications: samples were fixed with 4% paraformaldehyde (methanol-free) for 10 min at room temperature, washed twice with PBS for 5 min, and then incubated with 0.2% Triton X-100 for 15 min at room temperature. After two washes of 5 min each with PBS, the samples were incubated with equilibration buffer (from kit) for 10 min at room temperature. The equilibration buffer was drained, and reaction buffer containing equilibration buffer, nucleotide mix, and TdT enzyme was added to the tissue sections and incubated in a humid atmosphere at 37° C. for 1 h in the dark. The reaction was terminated by immersing the samples in 2×SSC for 15 min. Samples were washed 3 times for 5 min to remove unincorporated fluorescein-dUTP. For quantification of endothelial cells, the samples were incubated with 300 μg/ml of Hoechst stain for 10 min at room temperature. Fluorescent bleaching was minimized by treating slides with an enhancing reagent (Prolong solution). Immunofluorescence microscopy was performed using a 40× objective (Zeiss Plan-Neofluar) on an epifluorescence microscope equipped with narrow bandpass excitation filters mounted in a filter wheel (Ludl Electronic Products, Hawthorne, N.Y.) to individually select for green, red, and blue fluorescence.

Images were captured using a cooled CCD camera (Photometrics, Tucson, Ariz.) and SmartCapture software (Digital Scientific, Cambridge, England) on a Macintosh computer. Images were further processed using Adobe Photoshop software (Adobe Systems, Mountain View, Calif.). Endothelial cells were identified by red fluorescence, and DNA fragmentation was detected by localized green and yellow fluorescence within the nucleus of apoptotic cells. Quantification of apoptotic endothelial cells was expressed as an average of the ratio of apoptotic endothelial cells to total number of endothelial cells in 5–10 random 0.011 mm$^2$ fields at 400× magnification. For the quantification of total TUNEL expression, the number of apoptotic events was counted in 10 random 0.159-mm$^2$ fields at 100× magnification.

Quantification of Microvessel Density (MVD), PCNA, and Optical Density (OD). To quantify MVD, 10 random 0.159-mm$^2$ fields at 100× magnification were captured for each tumor, and microvessels were quantified according to the method described previously. To quantify the immunohistochemical reaction intensity, the OD of 100 VEGF- and IL-8-positive cells in 10 random 0.039-mm$^2$ fields at 200× magnification of treated tumor tissues was measured using Optimas Image Analysis software. The samples were not counterstained, so the OD was due solely to the product of the IHC reaction. VEGF and IL-8 cytoplasmic immunoreactivity was evaluated by computer-assisted image analysis and expressed as a ratio of tumor cell expression to normal pancreatic gland expression multiplied by 100 (Yoneda et al. 1998; Radinsky et al. 1995). To quantify PCNA expression, the number of positive cells were counted in 10 random 0.159-mm$^2$ fields at 100× magnification.

In Vitro Cytotoxicity Assay. In all assays, 700–1000 tumor cells were seeded into 38-mm$^2$ wells of flat-bottomed 96-well plates in quadruplicate and allowed to adhere overnight. The cultures were then washed and refed with medium (negative control) or medium containing PKI166 with or without gemcitabine. After 6 days (control cultures did not reach confluence), the number of metabolically active cells was determined by MTT assay (Fan et al. 1992). Following a 2–4 h incubation in medium containing 0.42 mg/ml of MTT, the cells were lysed in DMSO. The conversion of MTT to formazan by metabolically viable cells was monitored by an MR-5000 96-well microtiter plate reader at 570 nm (Dynatech, Inc., Chantilly, Va.). Growth inhibition was calculated from the formula:

Cytostasis (%)=[1−(A/B)]×100, where A is the absorbance of treated cells and B is the absorbance of the control cells.

Western Blot Analysis of EGF-R Autophosphorylation following Treatment with PKI166. Serum-starved L3.6pl cells were treated with PKI166 (0.01, 0.05, and 0.5 µM) for 60 min and then incubated with or without 40 ng/ml rhEGF for 10 min, washed, and scraped into PBS containing 5 mM EDTA and 1 mM Na Orthovanadate, and centrifuged, and the pellet resuspended in lysis buffer (20 mM Tris-HCl, pH 8.0, 137 mM NaCl, 10% glycerol, 2 mM EDTA, 1 mM phenylmethylsulfonyl fluoride, 20 µM leupeptin, and 0.15 U/ml aprotinin) sonicated, and centrifuged to recover insoluble protein. Immunoprecipitation was performed using Mab anti-EGF-R (clone EGF-RI) as described previously (Perrotte et al. 1999; Parker et al. 1998). Immunoprecipitates were analyzed on 7.5% NaDodSO$_4$-PAGE and transferred onto 0.45-µm nitrocellulose membranes. The filters were blocked with 3% bovine serum albumin in TDS (20 mM Tris-HCl, pH 7.5, 150 mM NaCl), probed with either polyclonal sheep anti-human EGF-R (1:1000) or monoclonal anti-phosphotyrosine (Mab 4G10) (1:2000) in TTBS (0.1% Tween 20 in TBS), and incubated with horseradish peroxidase-conjugated donkey anti-sheep IgG (1:2000) (Sigma Immunochemicals, St. Louis, Mo.) or sheep anti-mouse IgG (1:2000), respectively, in TTBS. Protein bands were visualized by ECL detection system. For an additional experiment, serum-starved L3.6pl cells were treated with gemcitabine (10 nM) with or without PKI166 (0.05, 0.5 µM) for 1 h, and then incubated with or without rhEGF (40 ng/ml) for 10 min. Western blot analysis was then carried out.

In vitro Expression of VEGF and IL-8. L3.6pl cells (2000 cells/38 mm$^2$ well) were plated into 96-well plates in 200 µl supplemented DMEM containing 5% FBS for 24 h, and then treated with 0.05, 0.5, or 1 µM PKI166. Supplemented DMEM (5% FBS) and human IgG (10 µg/ml) served as controls. Seventy-two hours later, the culture supernatants were collected, and the level of VEGF and IL-8 proteins (corrected for cell number) were determined by Quantikine ELISA kits.

Statistical Analysis. Pancreatic tumor volume, incidence of metastasis, expression of VEGF, IL-8, quantification of PCNA, TUNEL, CD3 1, and the percentage of apoptotic endothelial cells were compared by unpaired Student's t test. Survival analysis was computed by the Kaplan-Meier method and compared by the log-rank test.

RESULTS

In vitro Selectivity for Inhibition of Protein Kinases. PKI166 (4-(R)-phenethylamino-6-(4 hydroxy)phenyl-7H-pyrrolo[23-d]-pyrimidine), a novel EGF-R tyrosine kinase inhibitor of the pyrrolo-pyrimidine class, inhibited the intracellular domain (ICD) of the EGF-R kinase with an IC$_{50}$ value of 0.7 nM (Table 2). Enzyme kinetic studies support the idea that PKI166 affects the EGF-R kinase by ATP-competitive inhibition. PKI166 showed a high selectivity ratio of >3000 with respect to the inhibition of the serine/threonine kinases PKC-α and Cdc2/cyclin B. With respect to other tyrosine kinases, PKI166 was also active against the c-Abl tyrosine kinase (IC$_{50}$=28 nM) and showed some activity against c-Src (IC$_{50}$=130 nM) and the VEGF receptor family tyrosine kinases KDR (IC$_{50}$=327 nM) and Flt-1 (IC$_{50}$=962 nM). However, there was a selectivity factor of >40 for inhibition of the EGF-R ICD (Traxler et al. 1999). Following a single oral administration of 100 mg/kg to mice, PKI166 is rapidly absorbed (t max=1 h) and high concentrations of PKI166 are detected in the plasma (C max=32.8 µM) and in subcutaneous A431 tumors (C max=53.0 µM). Sustained levels of unchanged PKI166 are found in the plasma of mice up to 8 h after oral administration (Traxler et al. 1999).

TABLE 2

Relative Inhibition of Enzymatic Activity by PKI166$^\alpha$

| ENZYME | IC50[µM] |
|---|---|
| Tyrosine kinases | |
| EGF-R-ICD | 0.0007 |
| c-Src | 0.103 |
| c-Abl | 0.028 |
| KDR | 0.327 |
| Flt-1 | 0.962 |

TABLE 2-continued

Relative Inhibition of Enzymatic Activity by PK1166[a]

| ENZYME | IC50[μM] |
|---|---|
| Flk | >1 |
| c-Met | >1 |
| Tek | >1 |
| c-Kit | 2.210 |
| Serine/threonine kinases | |
| PKC-α | >100 |
| cdC2/cyclin B | 78 |

[a]Detailed descriptions are found in "Materials and Methods."

TABLE 3

Therapy of Human Pancreatic Carcinoma Growing in the Pancreas of Nude Mice

| Treatment Group[a] | Pancreatic Tumors | | | Metastasis | |
|---|---|---|---|---|---|
| | Incidence | Median | Range | Liver | Lymph Node |
| Saline Control | 10/10[b] | 399 | 116–123 | 3/10[b] | 9/10[b] |
| Gemcitabine | 10/10 | 166 | 61–273[c] | 1/10 | 9/10 |
| PK1166 | 10/10 | 220 | 61–361[c] | 1/10 | 9/10 |
| PK1166 + Gemcitabine | 10/10 | 59 | 9–119[d] | 1/10 | 6/10[c] |

[a]L3.6p1 human pancreatic cancer cells (1 × 10⁶ were injected into the pancreas of nude mice. Seven days later, groups of mice were treated with biweekly i.p. injections of gemcitabine (125 mg/kg) alone, daily oral feedings of PK1166 (100 mg/kg) alone, gemcitabine and PK1166, or saline (control). All mice were killed on day 35.
[b]Number of positive mice/number of mice receiving injections.
[c]$P < 0.001$ versus control.
[d]$P < 0.001$ versus all other groups.

TABLE 4

Survival of Nude Mice with Human Pancreatic Carcinoma by Therapy with PK1166 and Gemcitabine

| Treatment Group[a] | Pancreatic Tumors | Metastasis | | Survival (days) | |
|---|---|---|---|---|---|
| | | Liver | Lymph Nodes | Median | Range |
| Saline Control | 15/15[b] | 7/15 | 14/15 | 37 | 30–50 |
| Gemcitabine | 15/15 | 11/15 | 13/15 | 56 | 42–72 |
| PK1166 | 15/15 | 5/15 | 10/15 | 70 | 34–90[c] |
| PK1166 + gemcitabine | 10/15 | 0/15[c] | 4/15 | 75 | 30–100[c] |

[a]Nude mice received injections in the pancreas with 1 × 10⁶ L3.6p1 cells. Seven days later, groups of mice were treated with biweekly i.p. injections of gemcitabine (125 mg/kg), daily oral feedings of PK1166 (50 mg/kg), gemcitabine and PK1166, or saline (control). Moribund mice were killed and necropsied.
[b]Tumor-positive mice/mice receiving injections.
[c]$P < 0.0001$ as compared with other groups of mice.

TABLE 5

Immunohistochemical Analysis of Human Pancreatic Carcinoma in the Pancreas of Control and Treated Nude Mice

| Treatment Group[a] | Tumor Cells | | | | |
|---|---|---|---|---|---|
| | PCNA⁺ | TUNEL⁺ | VEGF | IL-8 | CD |
| Saline control | 237 ± 39[b] | 66 ± 21[b] | 338 ± 37[c] | 296 ± 46[c] | 60 |
| PK1166 | 185 ± 33 | 287 ± 84[e] | 173 ± 20[e] | 185 ± 11[e] | 24 |
| Gemcitabine | 237 ± 66 | 225 ± 95[e] | 298 ± 54 | 299 ± 43 | 52 |
| PK1166 + Gemcitabine | 130 ± 45[e] | 298 ± 80[e] | 156 ± 31[e] | 187 ± 35[e] | 24 |

[a]L3.6p1 human pancreatic cancer cells (1 × 10⁶) were injected into the pancreas of nude mice. Seven days later, groups of mice were trated with biweekly i.p. injections of gemcitabine (125 mg/kg) alone, daily oral feedings of PK1166 (100 mg/kg) alone, gemcitabine and PK1166, or saline (control). All mice were killed on day 35.
[b]Mean ± SD positive cells/field determined from measurement of 10 random 0.159-mm² fields at ×100.
[c]Mean ± SD absorbance determined as described in "Materials and Methods."
[d]Mean ± SD CD31/TUNEL-positive cells in 10 random 0.0011-mm² fields at ×400. Fluorescent double labeling was performed on frozen tissue sections.
[e]$P < 0.001$ as compared with controls.

Inhibition of EGF-R Autophosphorylation in Human Pancreatic Cancer Cells by PKI166. In the first set of experiments, ability of treatment of L3.6pl cells with PKI166 to inhibit EGF-stimulated tyrosine phosphorylation of the EGF-R were determined. L3.6pl cells incubated 15 min with medium free of serum but containing EGF exhibited high levels of autophosphorylated EGF-R (170-kDa band) as detected by antiphosphotyrosine antisera on Western blots of anti-EGF-R-immunoprecipitated cell lysates. Pretreatment of the cells with PKI166 for 60 min followed by a 15-min treatment with EGF inhibited the autophosphorylation in a dose-dependent manner (0.01–0.5 μM). The 170-kDa band was confirmed as EGF-R by Western blot analysis using anti-EGF-R antisera. Northern blot analysis demonstrated that the high levels of EGF-R-specific transcripts in the L3.6pl cells did not vary in response to the treatment. Gemcitabine at a concentration of 10 μM did not affect the autophosphorylation of EGF-R (data not shown).

In vitro Cytotoxicity Mediated by Gemcitabine and PKI166. L3.6pl cells were incubated for 6 days in medium containing increasing concentrations of gemcitabine (0–10 μM) in the absence or presence of a noncytostatic concentration of PKI166 (0.03 μM). The cytotoxicity mediated by gemcitabine was enhanced by PKI166, the IC$_{50}$ falling from 0.88 μM for gemcitabine to 0.52 μM (P<0.05)in the presence of PKI166.

Inhibition of Pancreatic Cancer Growth and Metastasis. Athymic nude mice were injected in the pancreas with L3.6pl cells. Seven days later, the mice were randomized into four treatment groups of 10 mice each. The first group received twice weekly i.p. injections of gemcitabine at 125 mg/kg, the second group received daily oral administrations of PKI166 at 100 mg/kg, a third group received twice weekly gemcitabine and daily PKI166, and the last group received HBSS as control. All mice were killed on day 35 because the control mice were moribund. Detailed necropsy revealed that all of the mice had tumors in the pancreas. The data summarized in Table 3 show that daily oral PKI166 or twice weekly i.p. injections of gemcitabine significantly decreased median tumor volume as compared to control mice (220, 166, and 399 mm³, respectively; P<0.01). The combination of gemcitabine and PKI166 produced a still greater decrease in pancreatic median tumor volume (59 mm³; P<0.0001). Visible liver metastases (enumerated with the aid of a dissecting microscope) were present in 30% of control mice and 10% of the treatment groups (Table 3). Histologically positive regional lymph node metastases were found in 90% of control animals, in 90% of gemcitabine-treated animals, and 90% of PKI166-treated animals. However, only 60% of animals receiving both gemcitabine and PKI166 had histologically positive regional lymph node metastases (Table 3). Treatments with PKI166 alone or in combination with gemcitabine were well tolerated as determined by maintenance of body weight (Table 3).

For a second survival study, the group size was increased to 15 mice. Mice were killed and necropsied when they became moribund, and the data summarized in Table 4. The median survival time in the control group was 37 days. Following treatment with gemcitabine alone, PKI166 alone, and combination therapy, the median survival time was 56, 70, and 75 days, respectively (control vs. gemcitabine, P<0.00002; control vs. PKI166, P<0.000001; control vs. PKI166 and gemcitabine, P<0.00001). Detailed necropsy revealed that all control mice or mice treated with only gemcitabine or only PKI166 had pancreatic tumors, whereas in mice receiving the combination regimen, tumor incidence was 75%. The incidence of liver metastasis in control mice, mice treated with gemcitabine alone, or PKI166 alone was 7/15, 11/15, and 5/15, respectively, but none of the mice treated with PKI166 and gemcitabine had visible liver metastases (P<0.0001). The incidence of histologically confirmed lymph node metastasis was 14/15, 13/15, and 10/15 for control mice, gemcitabine-treated, or PKI166 treated mice, respectively, but in mice given the combination regimen, the incidence was 4/15 (P<0.01). Increasing the dose of gemcitabine to 250 mg/kg and 500 mg/kg did not further reduce pancreatic tumor growth and metastasis compared to the dose of 125 mg/kg used in this study (data not shown).

Histology and Immunohistochemical Analyses. Tumors harvested from the different groups were processed for routine histology and immunohistochemical analyses. Tumors from mice treated with gemcitabine and PKI166 had necrotic zones and contained a large number of infiltrating cells. Immunohistochemistry using specific anti-EGF-R antibodies and antibodies specific against tyrosine-phosphorylated (activated) EGF-R demonstrated that tumors from all treatment groups expressed similar levels of EGF-R, whereas only tumors from control mice or mice treated with gemcitabine stained positive for activated EGF-R.

Cell proliferation was evaluated and apoptosis using anti-PCNA antibodies and the TUNEL method, respectively. The mean number of PCNA-positive tumor cells in control tumors was 237±39. Following therapy with gemcitabine or PKI166, it was 237±66 or 185±33, respectively (Table 5). The lowest number of PCNA-positive cells (130±45) was found in tumors of mice treated with both gemcitabine and PKI166 (P<0.001).

The mean number of TUNEL-positive cells was inversely related to PCNA positivity. In control tumors, it was 66±21, in gemcitabine-treated tumors, it was 225±95, in PKI166-treated tumors, it was 287±84, and in combination-treated tumors, it was 298±80 (control vs gemcitabine, P<0.04; control vs PKI166, P<0.003, control vs PKI166+gemcitabine, P<0.001). There was no significant difference in the number of TUNEL-positive tumor cells in tumors treated with gemcitabine or PKI166 alone as compared to tumors in the combination therapy group. The calculated ratio of PCNA-positive over TUNEL-positive cells was 1.1, 0.64, 0.43, and 3.61 in mice treated with gemcitabine alone, PKI166 alone, combination therapy, and control mice, respectively.

Tumor cell production of VEGF and IL-8 was significantly reduced (P<0.001) 35 days after initiation of treatment with PKI166 or PKI166 and gemcitabine as compared to gemcitabine alone or control mice (Table 5). To determine whether blockade of the EGF-R signaling pathway by PKI166 downregulated expression of VEGF and IL-8 by L3.6pl cells, cells were plated into wells and incubated the cells for 72 h in medium supplemented with 5% FBS with or without 1 μM PKI166 or 10 nM gemcitabine. The culture supernatants were harvested, and the level of VEGF and IL-8 proteins was determined by ELISA. Control cells produced 1400 pg/ml of VEGF and 1440 pg/ml IL-8. Gemcitabine-treated cells produced 1280 pg/ml VEGF and 2000 pg/ml IL-8. Cells treated with PKI166 produced 180 pg/ml VEGF (P<0.001) and 640 pg/ml IL-8 (P<0.01). Thus, blockade of the EGF-R signaling pathway decreased production of two important proangiogenic molecules. No effects were found for expression of bFGF protein (data not shown).

MVD (measured by staining with antibodies against CD31) was directly proportional to expression of VEGF and IL-8, i.e., a significant reduction in tumor MVD per field following treatment with PKI166 (24±18) or combination therapy (24±13) as compared to control tumors (60±23) or gemcitabine-treated tumors (52±18) (control vs PKI166, P<0.0005; control vs PKI166 and gemcitabine, P<0.0002) (Table 5) was observed. There was no significant difference in MVD of tumors treated with PKI166 alone as compared to tumors following combination therapy.

Finally, the CD31/TUNEL fluorescent double-labeling technique revealed that many endothelial cells in tumors treated with PKI166 or combination therapy were undergoing apoptosis. A significant increase in the percentage of apoptotic endothelial cells over total endothelial cells was found in pancreatic tumors harvested 23 days after the initiation of treatment with PKI166 (20±15) or PKI166+ gemcitabine (31±20) as compared to control tumors or gemcitabine-treated tumors (P<0.001) (Table 5).

EXAMPLE 3

Parallel Expression of Activated EGF-R in Neoplasms and Hair Follicles

C3H/HeN mice were injected subcutaneously with UV-2237 fibrosarcoma cells. Seven days after the implantation, the mice were given 3 weekley oral administrations of PBS, 10 mg/kg PKI166, 50 mg/kg PKI166, and 100 mg/kg PKI166. The mice were killed on day 15 of treatment (6 oral administrations), i.e., one day after the last oral administration.

Figure 8:
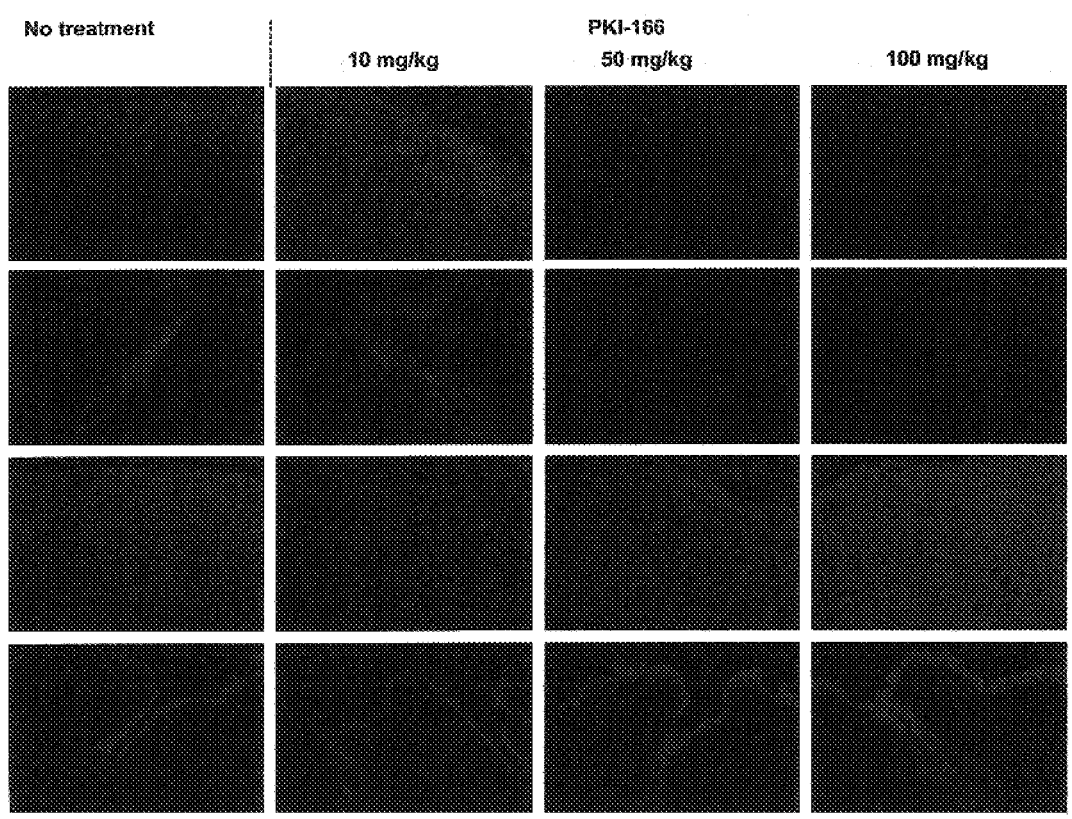
FIG. 8—Parallel expression level of activated EGF-R in neoplasms and hair follicles. Tumors and skin/hair samples were sectioned and stained with antibodies against the EGF-R and antibodies against the phosphorylated (activated) EGF-R.

The tumors were harvested and processed for immunohistochemistry. The contralateral dorsal skin and hair were excised and prepare for immunohistochemistry. The tumors and skin/hair samples were sectioned and stained with antibodies against the EGF-R and antibodies against the phosphorylated (activated) EGF-R. The results are shown in FIG. 8.

Regardless of the therapy, all tumor samples and all skin/hair follicle samples were positive for EGF-R. Oral therapy with 10 mg/kg PKI166 did not decrease expression of the activated EGF-R in tumors or skin/hair follicles. Oral treatment with 50 mg/kg or 100 mg/kg or PKI166 inhibited phosphorylation of the EGF-R in both tumors and skin/hair follicles.

Thus, the expression of phosphorylated EGF-R in skin/hair follicles parallels that of tumors. Determination of phosphorylated EGF-R in skin/hair follicles can therefore serve as a surrogate for tumors.

All of the compositions and/methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. REFERENCES

The following references, to the extent that they provide exemplary procedural or other details supplementary to those set forth herein, are specifically incorporated herein by reference.

Aboud-Pirak, E., Hurwitz, E., Pirak, M. E., Bellot, F., Schlessinger, J., and Sela, M. Efficacy of antibodies to epidermal growth factor receptor against KB carcinoma in vitro and in nude mice. *J. Nat'l Cancer Inst.*, 80:1605–1611, 1988.

Almoguera, C., Shibata, D., Forrester, K., Martin, J., Arnheim, N., and Perucho, M. Most human carcinomas of the exocrine pancreas contain mutant c-K-ras genes. *Cell*, 53:549–554, 1988.

Arion, D., Meijer, L., and Beach, D. Cdc-2 is a component of the M-phase specific histone 1 kinase: evidence for identity with MPF. *Cell*, 55:371–378, 1988.

Baselga, J., Norton, L., Masui, H., Pandiella, A., Coplan. K., Miller, W. H. J., and Mendelsohn, J. Antitumor effects of doxorubicin in combination with anti-epidermal growth factor receptor monoclonal antibodies. *J. Nat'l Cancer Inst.*, 85:1327–1333, 1993.

Benjamin, L. E., Golijanin, D., Itin, A., Pode, D., and Keshet, E. Selective ablation of immature blood vessels in established human tumors follows vascular endothelial growth factor withdrawal. *J. Clin. Invest.*, 103:159–165, 1999.

Benjamin, L. E., and Keshet, E. Conditioned switching of vascular endothelial growth factor (VEGF) expression in tumors: induction of endothelial cell shedding and regression of hemangioblastoma-like vessels by VEGF withdrawal. *Proc. Nat'l Acad. Sci. USA*, 94:8761–8766, 1997.

Bergmann, U., Funatomi, H., Yokoyama, M., Beger, H. G., and Korc, M. Insulin-like growth factor I overexpression in human pancreatic cancer: evidence for autocrine and paracrine roles. Cancer Res., 55:2007–2011, 1995.

Bhat, A., Kolibaba, K. S., Oda, T., Ohno-Jones, S., and Druker, B. J. Interactions of CBL with BCR-ABL and CRKL in BCR-ABL-transformed myeloid cells. *J. Biol. Chem.*, 272:16170–16175, 1997.

Bohling, T., Hatva. E., Kujala, M., Claesson-Welsh, L., Alitalo, K., and Haltia, M. Expression of growth factors and growth factor receptors in capillary hemangioblastoma. *J. Neuropathol. Exp. Neurol.*, 55:522–527, 1996.

Bruns, C. J., Harbison, M. T., Kuniyasu, H., Eue, I, and Fidler, I. J. In vivo selection and characterization of metastatic variants from human pancreatic adenocarcinoma by using orthotopic implantation in nude mice. *Neoplasia*, 1:50–62, 1999.

Burris, H. A., III, Moore, M. J., Andersen, J., Green, M. R., and Rothenberg, M. L. Improvements in survival and clinical benefit with gemcitabine as first-line therapy for patients with advanced pancreas cancer: a randomized trial. *J. Clin. Oncol.*, 15:2403–2413, 1997.

Caldas, C., Hahn, S., da Costa, L., Redston, M., Schutte, M., Seymour, A., Weinstein, C., Hruban, R., Yeo, C., and Kern, S. Frequent somatic mutations and homozygous deletions of the p16 (MTS1) gene in pancreatic adenocarcinoma. *Nat. Genet.*, 8:27–32, 1994.

Ciardiello, F., Damiano, V., Bianco, R., Bianco, C., Fontanini, C., De Laurentiis, M., De Placido, S., Mendelsohn, J., Bianco, A. R., and Tortora, G. Antitumor activity of combined blockade of epidermal growth factor receptor and protein kinase A. *J. Nat'l Cancer Inst.*, 88:1770–1776, 1996.

Ebert, M., Yokoyama, M., Kobrin, M. S., Friess, H., Lopez, M. E., Buchler, M. W., Johnson, G. R., and Korc, M. Induction and expression of amphiregulin in human pancreatic cancer. *Cancer Res.*, 54:3959–3962, 1994.

Evans, D. B., Abbruzzese, J. L., and Rich, T. R. Cancer of the pancreas. In: V. T. deVita, S. Hellman, and S. A. Rosenberg (eds.), CANCER: PRINCIPLES AND PRACTICE OF ONCOLOGY, $5^{th}$ edt., pp. 1054–1087. Philadelphia: J. B. Lippincott, 1997.

Fan, D., Poste, G., O'Brian, C. A., Seid, C., Ward, N. E., Earnest, L. E., and Fidler, I. J. Chemosensitization of murine fibrosarcoma cells to drugs affected by the multidrug resistance phenotype by the antidepressant trazodone: an experimental model for the reversal of intrinsic drug resistance. *Int. J. Oncol.*, 1:735–742, 1992.

Fernandez, E., La Vecchia, C., Porta, M., Negri, E., Lucchini, F., and Levi F. Trends in pancreatic cancer mortality in Europe, 1955–1989. *Int. J. Cancer*, 57:786–792, 1994.

Ferrara, N. The role of vascular endothelial growth factor in pathological angiogenesis. *Breast Cancer Res. Treat.*, 36:127–137, 1995.

Folkman, J. Angiogenesis in cancer, vascular, rheumatoid and other diseases. *Nat. Med.*, 1:27–31, 1995.

Geissler, J. F., Roesel, J. L., Meyer, T., Trinks, U. P., Traxler, P., and Lydon, N. B. Benzopyranones and benzothiopyranones: a class of tyrosine protein kinase inhibitors with selectivity for the v-Abl kinase. *Cancer Res.*, 52:4492–4498, 1992.

Geissler, J. F., Traxler, P., Regenass, U., Murray, B. J., Roesel, J. L., Meyer, T., McGlynn, E., Storni, A., and Lydon, N. B. Thiazolidine-diones: Biochemical and biological activity of a novel class of tyrosine protein kinase inhibitors. *J. Biol. Chem.*, 265:22255–22261, 1990.

Gerber, H. P., Dixit, V., and Ferrara, N. Vascular endothelial growth factor induces expression of the antiapoptotic proteins Bcl-2 and A1 in vascular endothelial cells. *J. Biol. Chem.*, 273:13313–13316, 1998.

Goldman, C. K., Kim, J., Wong, W. L., King, V., Brock, T., and Gillespie, G. Y. Epidermal growth factor stimulates vascular endothelial growth factor production by human malignant glioma cells: a model of glioblastoma multiforme pathophysiology. *Mol. Biol. Cell*, 4:121–133, 1993.

Grau, A. M., Zhang, L., Wang, W., Evans, D. B., Abbruzzese, J. L., and Chiao, P. J. Induction of $P21^{waf1}$ expression and growth inhibition by transforming growth factor-β is mediated by the tumor suppressor gene DPC-4 in human pancreatic adenocarcinoma cells. *Cancer Res.,* 57:3929–3934, 1997.

Grugel, S., Finkenzeller, G., Weindel, K., Barleon, B., and Marme, D. Both v-Ha-Ras and v-Raf stimulate expression of the vascular endothelial growth factor in NIH 3T3 cells. *J. Biol. Chem.,* 270:25915–25919, 1995.

Hahn, S. A., Schutte, M., Hoque, A. T., Moskaluk, C. A., da Costa, L. T., Rozenblum, E., Weinstein, C. L., Fisher, A., Yeo, C. J., Hruban, R. H., and Kern, S. E. DPC4, A candidate tumor suppressor gene at human chromosome 18q21.1. *Science,* 271:350–353, 1996.

Hanahan, D., and Folkman, J. Patterns and emerging mechanisms of the angiogenic switch during tumorigenesis. *Cell,* 86:353–364, 1996.

Huang, S. M., Bock, J. M., and Harari, P. M. Epidermal growth factor receptor blockade with C225 modulates proliferation, apoptosis, and radiosensitivity in squamous cell carcinomas of the head and neck. *Cancer Res.,* 59:1935–1940, 1999.

Kerbel, R. S., Viloria-Petit, A., Okada, F., and Rak, J. Establishing a link between oncogenes and tumor angiogenesis. *Mol. Med.,* 4:286–295, 1998.

Kitadai, Y., Haruma, K., Sumii, K., Yamamoto, S., Ue, T., Yokozaki, H., Yasui, W., Ohmoto, Y., Fidler, I. J., Tahara, E., and Kajiyama, G. Expression of interleukin-8 correlates with vascularity in human gastric carcinomas. *Am. J. Pathol.,* 152:93–100, 1998.

Kobrin, M. S., Funatomi, H., Friess, H., Buchler, M. W., Stathis, P., and Korc, M. Induction and expression of heparin-binding EGF-like growth factor in human pancreatic cancer. *Biochem. Biophys. Res. Commun.,* 202: 1705–1709, 1994.

Korc, M., Chandrasekar, B, Yamanaka, Y., Friess, H., Buchier, M., and Beger, H. G. Overexpression of the epidermal growth factor receptor in human pancreatic cancer is associated with concomitant increases in the levels of epidermal growth factor and transforming growth factor alpha *J. Clin. Invest.,* 90:1352–1360, 1993.

Kumar, R., Yoneda, J., Bucana, C. D., and Fidler, I. J. Regulation of distinct steps of angiogenesis by different angiogenic molecules. *Int. J. Oncol.,* 12:749–757, 1998.

Kuniyasu, H., Ellis, L. M., Evans, D. B., Abbruzzese, J. L., Fenoglio, C. J., Bucana, C. D., Cleary, K. R., Tahara, E., and Fidler, I. J. Relative expression of E-cadherin and type IV collagenase genes predicts disease outcome in patients with resectable pancreatic carcinoma. *Clin. Cancer Res.,* 5:25–33, 1999.

Landis, S. H., Murray, T., Bolden, S., and Wingo, P. A. Cancer statistics, 1999. *CA: A Cancer J. Clin.,* 49:8–31, 1999.

Lipson, K. E., Pang, L., Huber, L. J., Chen, H., Tsai, J. M., Hirth, P., Gazit, A., Levitzki, A., and McMahon, G. Inhibition of platelet-derived growth factor and epidermal growth factor receptor signaling events after treatment of cells with specific synthetic inhibitors of tyrosine kinase phosphorylation. *J. Pharmaco. Exp. Ther.,* 285:844–852, 1998.

Massague, J., and Pandiella, A. Membrane-anchored growth factors. *Annu. Rev. Biochem.,* 62: 515–541, 1993.

McGlynn, E., Becker, M., Mett, H., Reutener, S., Cozens, R., and Lydon, N. B. Large scale purification and characterization of a recombinant epidermal growth factor receptor protein-tyrosine kinase. *Eur. J. Biochem.,* 207: 265–275, 1992a.

McGlynn, E., Liebetanz, J., Reutener, S., Wood, J., Lydon, N. B., Hofstetter, H., Vanek, M., Meyer, T., and Fabbro, D. Expression and partial characterization of rat protein kinase C and protein kinase C in insect cells using recombinant baculovirus. *J. Cell. Biochem.,* 49:239–250, 1992b.

Mendelsohn, J. Epidermal growth factor receptor inhibition by a monoclonal antibody as anticancer therapy. *Clin. Cancer Res.,* 3:2703–2707, 1997.

Morgan, R. T., Woods, L. K., Moore, G. E., Quinn, L. A., McGavran, L., and Gordon, S. G. Human cell line (COLO375) of metastatic pancreatic adenocarcinoma. *Int. J. Cancer,* 25:591–598, 1980.

Nor, J. E., Christensen, J., Mooney, D. J., and Polverini, P. J. Vascular endothelial growth factor (VEGF)-mediated angiogenesis is associated with enhanced endothelial cell survival and induction of Bcl-2 expression. *Am. J. Pathol.,* 154:375–384, 1999.

Parker, C., Roseman, B. J., Bucana, C. D., Tsan, R., and Radinsky, R. Preferential activation of the epidermal growth factor receptor in human colon carcinoma liver metastases in nude mice. *J. Histochem. Cytochem.,* 46:595–602, 1998.

Partanen, J., Armstrong, E., Bergman, M., Makela, T. P., Hirvonen, H., Huebner, K., and Alitalo, K. Cyl encodes a putative cytoplasmic tyrosine kinase lacking the conserved tyrosine autophosphorylation site (Y416 src). *Oncogene,* 6:2013–2018, 1991.

Pazin, M. J., and Williams, L. T. Triggering signaling cascades by receptor tyrosine kinases. *Trends Biochem. Sci.,* 17:374–378, 1992.

Pellegata, N., Sessa, F., Renault, B., Bonto, M., Leone, B., Solicia, E., and Ranzani, G. K-ras and p53 gene mutations in pancreatic cancer: ductal and nonductal tumors progress through different genetic lesions. *Cancer Res.,* 54:1556–1560, 1994.

Perrotte, P., Matsumoto, T., Inoue, K., Kuniyasu, H., Eve, B. Y., Hicklin, D. J., Radinsky, R., and Dinney, C. P. Anti-epidermal growth factor receptor antibody C225 inhibits angiogenesis in human transitional cell carcinoma growing orthotopically in nude mice. *Clin. Cancer Res.,* 5:257–265, 1999.

Petit, A. M., Rak, J., Hung, M. C., Rockwell, P., Goldstein, N., Fendly, B., and Kerbel, R. S. Neutralizing antibodies against epidermal growth factor and ErbB-2/neu receptor tyrosine kinases down-regulate vascular endothelial growth factor production by tumor cells in vitro and in vivo: angiogenic implications for signal transduction therapy of solid tumors. *Am. J. Pathol.,* 151:1523–1530, 1997.

Radinsky, R., Risin, S., Fan, D., Dong, Z., Bielenberg, D., Bucana, C. D., and Fidler, I. J. Level and function of epidermal growth factor receptor predict the metastatic potential of human colon carcinoma cells. *Clin. Cancer Res.,* 1:19–31, 1995.

Rak, J., Filmus, J., and Kerbel, R. S. Reciprocal paracrine interactions between tumour cells and endothelial cells: the 'angiogenesis progression' hypothesis. *Eur. J. Cancer,* 32A:2438–2450, 1996.

Rak, J., Mitsuhashi, Y., Bayko, L., Filmus, J., Shirasawa, S., Sasazuki, T., and Kerbel, R. S. Mutant ras oncogene upregulates VEGF/VPF expression: implications for induction and inhibition of tumor angiogenesis. *Cancer Res.,* 55:4575–4580, 1995.

Rockwell, P., O'Connor, W. J., King, K., Goldstein, N. I., Zhang, L. M., and Stein, C. A. Cell-surface perturbations of the epidermal growth factor and vascular endothelial growth factor receptors by phosphorothioate oligodeoxynucleotides. *Proc. Nat'l Acad. Sci. USA,* 94:6523–6528, 1997.

Rozakis-Adcock, M., Fernley, R., Wade, J., Pawson, T., and Bowtell, D. The SH2 and SH3 domains of mammalian Grb2 couple the EGF receptor to the Ras activator mSos1. *Nature (Lond.),* 363:83–85, 1993.

Schreiber, A. B., Winkler, M. E., and Derynck, R. Transforming growth factor-α: a more potent angiogenic mediator than epidermal growth factor. *Science,* 232: 1250–1253, 1986.

Shi, S. R., Key, M. E., and Kalra, K. L. Antigen retrieval in formalin-fixed, paraffin-embedded tissues: an enhancement method for immunohistochemical staining based on microwave oven heating of tissue sections. *J. Histochem. Cytochem.,* 39:741–748, 1991.

Shiurba, R. A., Eng, L. F., Vogel, H., Lee, Y. L., Horoupian, D. S., and Urich, H. Epidermal growth factor receptor in meningiomas is expressed predominantly on endothelial cells. *Cancer,* 62:2139–2144, 1988.

Sinicrope, F. A., Evans, D. B., Leach, S. D., Cleary, K. R., Fenoglio, C. J., Lee, J. J., and Abbruzzese, J. L. Bcl-2 and p53 expression in resectable pancreatic adenocarcinomas-association with clinical outcome. *Clin. Cancer Res.,* 2:2015–2022, 1996.

Smith, J. J., Derynck, R., and Korc, M. Production of transforming growth factor alpha in human pancreatic cancer cells: evidence for a superagonist autocrine cycle. *Proc. Nat'l Acad. Sci. USA,* 84:7567–7570, 1987.

Syridopoulos, I., Brogi, E., Kearney, M., Sullivan, A. B., Cetrulo, C., Isner, M., and Losordo, D. W. Vascular endothelial growth factor inhibits endothelial cell apoptosis induced by tumor necrosis factor-alpha: balance between growth and death signals. *J. Mol. Cell Cardiol.,* 29:1321–1330, 1997.

Traxler, P., Buchdunger, E., Furet, P., Gschwind, H-P., Ho, P., Mett, H., O'Reilly, T., Pfaar, U., and Thomas, H. Preclinical profile of PKI166—a novel and potent EGF-R tyrosine kinase inhibitor for clinical development (abstract). *Clin. Cancer Res. (Suppl.),* 5(11):3750s, 1999.

Uckun, F. M., Narla, R. K., Jun, X., Zeren, T., Venkatachalam, T., Waddick, K. G., Rostostev, A., and Myers, D. E. Cytotoxic activity of epidermal growth factor-genistein against breast cancer cells. *Clin. Cancer Res.,* 4:901–912, 1998a.

Uckun, F. M., Narla, R. K., Zeren, T., Yanishevski, Y., Myers, D. E., Waurzyniak, B., Ek, O., Schneider, E., Messinger, Y., Chelstrom, L. M., Gunther, R., and Evans, W. In vivo toxicity, pharmacokinetics, and anticancer activity of Genistein linked to recombinant human epidermal growth factor. *Clin. Cancer Res.,* 4:1125–1134, 1998b.

Ullrich, A., Coussens, L., Hayflick, J. S., Dull, T. J., Gray, A., Tam, A. W., Lee, J., Yarden, Y., Libermann, T. A., and Schlessinger, J. Human epidermal growth factor receptor cDNA sequence and aberrant expression of the amplified gene in A431 epidermoid carcinoma cells. *Nature,* 309: 418–425, 1984.

van Gog, F. B., Brakenhoff, R. H., and Stigter-van Snow, G. B. Perspectives of combined radioimmunotherapy and anti-EGFR antibody therapy for the treatment of residual head and neck cancer. *Int. J. Cancer,* 77:13–18, 1998.

Vezeridis, M. P., Tzanakakis, G. N., Meitner, P. A., Doremus, C. M., and Tibbetts, L. M. In vivo selection of a highly metastatic cell line of a human pancreatic carcinoma in the nude mouse. *Cancer,* 69:2060–2063, 1992.

Wagner, M., Cao, T, Lopez, M. E., Hope, C., van Nostrand, K., Kobrin, M. S., Fan, H. U., Buchler, M. W., and Korc, M. Expression of a truncated EGF receptor is associated with inhibition of pancreatic cancer cell growth and enhanced sensitivity to cisplatinum. *Int. J. Cancer,* 68:782–787, 1996.

Wagner, M., Lopez, M. E., Cahn, M., and Korc, M. Suppression of fibroblast growth factor receptor signaling inhibits pancreatic cancer growth in vitro and in vivo. *Gastroenterology,* 114:798–807, 1998.

Wanebo, H. J., and Vezeridis, M. P. Pancreatic carcinoma in perspective: a continuing challenge. *Cancer,* 78: 580–591, 1996.

Warshaw, A. L., and Fernandez-del Castillo, C. Pancreatic carcinoma. *N. Engl. J Med.,* 326:455–465, 1992.

Watanabe, Y., and Dvorak, H. V. Vascular permeability factor/vascular endothelial growth factor inhibits anchorage-disruption-induced apoptosis in microvessel endothelial cells by inducing scaffold formation. *Exp. Cell Res.,* 233:340–349, 1997.

Weidner, N., Semple, J. P., Welch, W. R., and Folkman, J. Tumor angiogenesis and metastasis—correlation in invasive breast carcinoma. *N. Engl. J Med.,* 324:1–8, 1991.

Xu, L., Xie, K., Mukaida, N., Matsushima, K., and Fidler, I. J. Hypoxia-induced elevation in interleukin-8 expression by human ovarian carcinoma cells. *Cancer Res.,* 59:5822–5829, 1999.

Yamanaka, Y., Friess, H., Kobrin, M. S., Buchler, M., Beger, H. G., and Korc, M. Coexpression of epidermal growth factor receptor and ligands in human pancreatic cancer is associated with enhanced tumor aggressiveness. *Anticancer Res.,* 13:565–569, 1993a.

Yamanaka, Y., Friess, H., Kobrin, M. S., Buchler, M., Kunz, J., Beger, H. G., and Korc, M. Overexpression of HER2/neu oncogene in human pancreatic carcinoma. *Hum. Pathol.,* 24:1127–1134, 1993b.

Yoneda, J., Kuniyasu, H., Crispens, M. A., Price, J. E., Bucana, C. D., and Fidler, I. J. Expression of angiogenesis-related genes and progression of human ovarian carcinomas in nude mice. *J. Nat'l Cancer Inst.,* 90:447–454, 1998.

What is claimed is:

1. A method for determining the effectiveness of a cancer treatment comprising:
   (a) obtaining non-tumor skin, mucosal or hair follicle tissue samples by non-invasive procedures from a patient before and after a patient undergoes cancer treatment with a chemotherapeutic agent, wherein i) said cancer overexpress epidermal growth factor receptor, ii) said cancer treatment is directed to said growth factor receptor, and iii) said chemotherapeutic agent is a protein kinase inhibitor that reduces phosphorylation of said growth factor receptor;
   (b) determining growth factor receptor phosphorylation in said tissues; and
   (c) comparing the growth factor receptor phosphorylation in the tissue obtained before treatment to the growth factor receptor phosphorylation in the tissue obtained after treatment, wherein a reduction of growth factor receptor phosphorylation in the tissue obtained after treatment as compared to that in the tissue obtained before treatment is indicative of the effectiveness of the cancer treatment.

2. The method of claim 1, wherein said tissue sample is a hair follicle.

3. The method of claim 1, wherein said tissue sample comprises buccal mucosa tissue.

4. The method of claim 1, wherein said tissue sample comprises a pap-smear sample.

5. The method of claim 1, wherein said tissue sample comprises bladder-wash cells.

6. The method of claim 1, wherein said tissue sample comprises skin scrapings.

7. The method of claim 1, wherein determining growth factor receptor phosphorylation comprises:
   (a) contacting the samples with an anti-phosphorylated growth factor receptor antibody;
   (b) detecting the bound antibody.

8. The method of claim 7, wherein the antibody further comprises a detectable label.

9. The method of claim 7, wherein the bound antibody is detected with a second antibody that comprises a detectable table.

10. The method of claims 8 or 9 wherein the detectable label is selected from a group comprising a fluor, an enzyme, or a radionuclide.

11. The method of claim 7 wherein said detecting comprises immunoflourescence.

12. The method of claim 7, wherein said detecting comprises colorimetric detection.

13. The method of claim 1, wherein the patient has cancer of the breast, prostrate, colon, pancreas, head and neck, bladder, blood, bone, bone marrow, esophagus, gastrointestine, brain, kidney, liver, lung, nasopharynx, ovary, skin, stomach, or uterus.

14. The method of claim 1, wherein said protein kinase inhibitor is a tyrosine kinase inhibitor.

15. The method of claim 14, wherein said chemotherapeutic agent is PKI166.

16. The method of claim 15, wherein said chemotherapeutic agent is the C225 antibody.

* * * * *

UNITED STATES PATENT AND TRADEMARK OFFICE
CERTIFICATE OF CORRECTION

PATENT NO. : 7,344,829 B2  
APPLICATION NO. : 10/010763  
DATED : March 18, 2008  
INVENTOR(S) : Isaiah J. Fidler et al.

Page 1 of 1

It is certified that error appears in the above-identified patent and that said Letters Patent is hereby corrected as shown below:

In title page, item (56) References Cited - U.S. Patent Documents, please insert:

--5,340,744  8/94  Lavker et al.  436/63  
5,427,916  6/95  Gewirtz et al.  435/6  
5,480,968  1/96  Kraus et al.  530/326  
5,599,681  2/97  Epstein et al.  435/7.23--.

In claim 1, column 46, line 49, please delete "overexpress" and insert --overexpresses-- therefor.

In claim 9, column 47, line 16, please delete "table" and insert --label-- therefor.

In claim 10, column 47, line 17, after "9", please insert --,--.

In claim 11, column 48, line 1, after "7", please insert --,--.

In claim 16, column 48, line 16, please delete "15" an insert --14-- therefor.

Signed and Sealed this

Eighth Day of July, 2008

JON W. DUDAS  
*Director of the United States Patent and Trademark Office*